US009144800B2

(12) United States Patent
Koeda

(10) Patent No.: US 9,144,800 B2
(45) Date of Patent: *Sep. 29, 2015

(54) THERMAL CYCLER AND THERMAL CYCLE METHOD

(75) Inventor: Hiroshi Koeda, Suwa (JP)

(73) Assignee: Seiko Epson Corporation (JP)

( * ) Notice: Subject to any disclaimer, the term of this patent is extended or adjusted under 35 U.S.C. 154(b) by 167 days.

This patent is subject to a terminal disclaimer.

(21) Appl. No.: 13/880,224

(22) PCT Filed: Nov. 29, 2011

(86) PCT No.: PCT/JP2011/006652

§ 371 (c)(1),
(2), (4) Date: Apr. 18, 2013

(87) PCT Pub. No.: WO2012/073484

PCT Pub. Date: Jun. 7, 2012

(65) Prior Publication Data

US 2013/0210081 A1 Aug. 15, 2013

(30) Foreign Application Priority Data

Dec. 1, 2010 (JP) ................................ 2010-268090

(51) Int. Cl.

*C12P 19/34* (2006.01)
*B01L 7/00* (2006.01)
*B01L 3/00* (2006.01)

(52) U.S. Cl.

CPC . *B01L 7/52* (2013.01); *B01L 7/525* (2013.01); *B01L 3/5082* (2013.01); *B01L 2200/0673* (2013.01); *B01L 2400/0457* (2013.01)

(58) Field of Classification Search

CPC ................ B01L 2200/0673; B01L 2400/0457; B01L 3/5082; B01L 7/52; B01L 7/525

USPC ............................................. 435/283.1, 91.2

See application file for complete search history.

(56) References Cited

U.S. PATENT DOCUMENTS

| | | | |
|---|---|---|---|
| 2005/0153430 | A1 | 7/2005 | Ohtaka |
| 2006/0083667 | A1 | 4/2006 | Kohara et al. |
| 2007/0039866 | A1 | 2/2007 | Schroeder et al. |
| 2009/0148912 | A1 | 6/2009 | Takagi |
| 2009/0197274 | A1 | 8/2009 | Takagi |
| 2011/0183378 | A1 | 7/2011 | Takagi et al. |
| 2012/0184025 | A1 | 7/2012 | Kawata et al. |

FOREIGN PATENT DOCUMENTS

| | | | |
|---|---|---|---|
| EP | 1788095 | A1 | 5/2007 |
| EP | 2465608 | A2 | 6/2012 |
| JP | 2006-110523 | A | 4/2006 |
| JP | 2009136250 | A | 6/2009 |
| WO | WO-2005016532 | A2 | 2/2005 |
| WO | WO-2008139415 | A1 | 11/2008 |
| WO | WO-2012-073484 | A1 | 6/2012 |

OTHER PUBLICATIONS

Extended European Search Report for Application No. EP 12 15 7455 dated Feb. 3, 2014 (8 pages).

*Primary Examiner* — Cynthia B Wilder

(74) *Attorney, Agent, or Firm* — Harness, Dickey & Pierce, P.L.C.

(57) ABSTRACT

A thermal cycler (1) includes a holder (11) that holds a biotip (100) filled with a reaction mixture and liquid having a smaller specific gravity than the reaction mixture and being immiscible with the reaction mixture, the biotip (100) including a channel (110) in which the reaction mixture moves, a heating unit (12) that heats a first portion (111) of the channel when the biotip (100) is in the holder (11), and a driving unit (20) that disposes the holder (11) and the heating unit (12) by making a switch between a first disposition and a second disposition, the first disposition being such that the first portion (111) is in a lowest part of the channel (110) with respect to a gravitational force direction when the biotip (100) is in the holder (11), the second disposition being such that a second portion (112) that is a different portion from the first portion (111) relative to a moving direction of the reaction mixture is in the lowest part of the channel (110) with respect to the gravitational force direction when the biotip (100) is in the holder (11).

20 Claims, 11 Drawing Sheets

| COMPOSITION | PRESERVATIVE CONCENTRATION | FINAL CONCENTRATION | DILUTION | ADDITIVE AMOUNT (uL) |
|---|---|---|---|---|
| One Step SYBR RT-PCR Buffer | 2x | 1x | 2 | 10uL |
| TaKaRa Ex Taq HS Mix | | | 16.6 | 1.2uL |
| PrimeScript PLUS RTase Mix | | | 50 | 0.4uL |
| Albumin Forward Primer | 10μM | 0.4μM | 25 | 0.8uL |
| Albumin Reverse Primer | 10μM | 0.4μM | 25 | 0.8uL |
| RNase Free $dH_2O$ | | | | 4.8uL |
| Total RNA | | | | 2uL |
| Total | | | | 20uL |

・TaKaRa Ex Taq is a registered trademark.

Fig. 12A

| NUMBER | BEFORE REACTION | AFTER REACTION | BRIGHTNESS CHANGE RATIO (%) |
|---|---|---|---|
| 1 | 7.1 | 32.2 | 354 |
| 2 | 7.2 | 32.3 | 349 |
| 3 | 7.7 | 34.0 | 342 |
| 4 | 7.2 | 31.4 | 336 |
| 5 | 7.1 | 34.3 | 383 |
| 6 | 7.3 | 34.2 | 368 |
| 7 | 7.3 | 32.1 | 340 |
| 8 | 7.3 | 35.6 | 388 |
| 9 | 7.6 | 36.2 | 376 |
| 10 | 7.7 | 34.1 | 343 |
| 11 | 7.2 | 32.5 | 351 |
| 12 | 7.6 | 35.2 | 363 |
| 13 | 7.5 | 35.0 | 367 |
| 14 | 7.5 | 36.8 | 391 |

Fig. 12B

| NUMBER | BEFORE REACTION | AFTER REACTION | BRIGHTNESS CHANGE RATIO (%) |
|---|---|---|---|
| 1 | 405982 | 1704615 | 320 |
| 2 | 448594 | 1755216 | 291 |
| 3 | 390663 | 2333047 | 497 |

THERMAL CYCLER AND THERMAL CYCLE METHOD

CROSS-REFERENCE TO RELATED APPLICATIONS

This is a U.S. National Stage Application of International Application No. PCT/JP2011/006652, filed Nov. 29, 2011 and published in English as WO 2012/073484 on Jun. 7, 2012. This application claims the benefit of Japanese Application No. 2010-268090, filed Dec. 1, 2010. The disclosures of the above applications are incorporated herein by reference.

TECHNICAL FIELD

This patent application is based upon and claims the benefit of priority of the prior Japanese Patent Application No. 2010-268090, filed Dec. 1, 2010, the entire contents of which are incorporated herein by reference.

The present invention relates to a thermal cycler and a thermal cycle method.

BACKGROUND ART

In recent years, with the advancement in utilization of genetic technology, medical treatment that involves utilization of genes, such as genetic diagnosis or gene therapy, has received attention, and also in the agricultural and livestock industry, a great number of methods involving utilization of genes for breed discrimination and cultivar improvement have been developed. As one kind of technologies utilizing genes, the PCR (Polymerase Chain Reaction) method is widely known. The PCR method is now a critical technology to elucidate the information on biological matters.

In the PCR method, a thermal cycle is applied to solution (reaction mixture) that includes a nucleic acid sequence subjected to amplification (target DNA) and a reagent in order to amplify the target DNA. A thermal cycle is a process to apply two or more stages of temperature to the reaction mixture and to repeat the cycle periodically. In the PCR method, usually two or three stages of temperature are applied in a thermal cycle.

In the PCR method, containers, namely tubes or biological sample reaction chips (biotips), for processing biochemical reaction are generally used. However, the known methods have disadvantageously required a large amount of reagent or other liquids for appropriate reaction, complicated the structure of apparatuses to realize thermal cycles necessary for the reaction, and taken a long period of time for the reaction. Thus, biotips or reaction apparatuses that realize PCR that is accurate, requires a shorter period of time, and uses a minimized amount of reagent and sample, have been desired.

To overcome such disadvantages, JP-A-2009-136250 discloses a biological sample reaction chip in which a reaction mixture and liquid that has a smaller specific gravity than the reaction mixture and is immiscible with the reaction mixture (such as mineral oil, hereinafter referred to as "liquid") are filled, and a biological sample reaction apparatus that applies thermal cycles by rotating the biological sample reaction chip around the horizontal rotational axis thereby moving the reaction mixture.

SUMMARY OF INVENTION

Technical Problem

The biological sample reaction apparatus disclosed in the JP-A-2009-136250 applies thermal cycles to the reaction mixture by continuously rotating the biological sample reaction chip. However, the reaction mixture moves in a chamber of the biological sample reaction chip along the continuous rotation and hence the chamber of the biological sample reaction chip is structurally made complex in order to keep the reaction mixture at a desired temperature for a desired period of time.

Solution to Problem

An advantage of some aspects of the present invention is to provide a thermal cycler and a thermal cycle method that facilitate control of a heating time period.

Application Example 1

A thermal cycler of the present application example includes a holder that holds a biotip filled with a reaction mixture and liquid having a smaller specific gravity than the reaction mixture and being immiscible with the reaction mixture, the biotip including a channel in which the reaction mixture moves in proximity to internal facing wall sections, a heating unit that heats a first portion of the channel when the biotip is in the holder, and a driving unit that disposes the holder and the heating unit by making a switch between a first disposition and a second disposition. The first disposition is such that the first portion is in a lowest part of the channel with respect to a gravitational force direction when the biotip is in the holder, and the second disposition is such that a second portion of the channel that is a different portion from the first portion relative to a moving direction of the reaction mixture is in the lowest part of the channel with respect to the gravitational force direction when the biotip is in the holder.

The thermal cycler of the present application example switches the disposition of the holder, thereby making a switch between a condition in which the biotip is held in the first disposition and a condition in which the biotip is held in the second disposition. The first disposition is such that the first portion of the channel constituting the biotip is in the lowest part of the channel with respect to the gravitational force direction. The second disposition is such that the second portion, which is a different portion from the first portion relative to the moving direction of the reaction mixture, is in the lowest part of the channel with respect to the gravitational force direction. In other words, the reaction mixture is kept within the first portion in the first disposition and within the second portion in the second disposition due to the gravitational force. The first portion is heated by the heating unit, and because the second portion is a different portion from the first portion relative to the moving direction of the reaction mixture, the temperatures of the first portion and the second portion differ. Therefore, while the biotip is held in the first disposition or in the second disposition, the reaction mixture is kept at a predetermined temperature, and hence a thermal cycler that is able to readily control a heating time period is provided.

Application Example 2

In the thermal cycler of the above application example, the driving unit may rotate the holder and the heating unit in one direction when switching from the first disposition to the second disposition and in the opposite direction when switching from the second disposition to the first disposition.

The thermal cycler in the present application example rotates the holder and the heating unit in the one direction when switching from the first disposition to the second disposition, and in the opposite direction when switching from the second disposition to the first disposition, thereby reducing the possibilities of the wiring of the cycler getting kinked as a result of the rotation. As such, damage is barely caused to the wiring in the cycler, and hence reliability of its thermal cycles is improved.

Application Example 3

In the thermal cycler of any of the above application examples, the driving unit may make a switch from the first disposition to the second disposition when a first period of time has passed while keeping the first disposition, and may make a switch from the second disposition to the first disposition when a second period of time has passed while keeping the second disposition.

The thermal cycler in the present application example switches a disposition from the first disposition to the second disposition when the first period of time has passed while keeping the first disposition and switches a disposition from the second disposition to the first disposition when the second period of time has passed while keeping the second disposition, thereby enabling to control more accurately the heating time periods of the reaction mixture in the first disposition or in the second disposition. Hence, it enables more accurate thermal cycles to be applied to the reaction mixture.

Application Example 4

In the thermal cycler of any of the above application examples, the holder may hold the biotip in which the reaction mixture moves in a longitudinal direction of the channel, the first portion may be a portion that includes one end of the channel in the longitudinal direction, and the second portion may be a portion that includes the other end of the channel in the longitudinal direction.

In the thermal cycler of the present application example, when the biotip, in which the reaction mixture moves in the longitudinal direction of the channel, is in the holder, a portion including the one end of the channel in the longitudinal direction is the first portion, and a portion including the other end of the channel in the longitudinal direction is the second portion. Thus, even when using the biotip having a simply structured channel, a thermal cycler that is able to readily control heating time periods.

Application Example 5

The thermal cycler of any of the above application examples may further include a second heating unit that heats the second portion when the biotip is in the holder, and the heating unit may heat the first portion to a first temperature and the second heating unit may heat the second portion to a second temperature that is different from the first temperature.

The thermal cycler of the present application example includes, the second heating unit that heats the second portion to the second temperature when the biotip is in the holder, thereby enabling to control more accurately the temperature of the first portion and the second portion of the biotip. Thus, it enables more accurate thermal cycles to be applied to the reaction mixture.

Application Example 6

In the thermal cycler of the preceding application example, the first temperature may be higher than the second temperature.

In the thermal cycler of the present application example, the first temperature is higher than the second temperature, and hence, when the biotip is in the holder, the first portion and the second portion of the biotip can be controlled to the temperatures appropriate for the thermal cycles. Thus, it enables appropriate thermal cycles to be applied to the reaction mixture.

Application Example 7

With the thermal cycler of the preceding application example, the first period of time may be shorter than the second period of time.

In the thermal cycler of the present application example, the first period of time is shorter than the second period of time, thereby enabling, when the biotip is in the holder, to differ heating time periods for heating the biotip at the first temperature and at the second temperature. Thus, when conducting a reaction that requires differing heating time periods for heating at the first temperature and at the second temperature, it enables appropriate thermal cycles to be applied to the reaction mixture.

Application Example 8

A thermal cycle method of the present application example includes placing in a holder a biotip that is filled with a reaction mixture and liquid having a smaller specific gravity than the reaction mixture and being immiscible with the reaction mixture, and has a channel in which the reaction mixture moves in proximity to internal facing wall sections, disposing the biotip in a first disposition in which a first portion of the channel is in a lowest part of the channel with respect to a gravitational force direction, heating the first portion of the channel, and disposing the biotip in a second disposition in which a second portion of the channel that is a different portion from the first portion relative to a moving direction of the reaction mixture is in the lowest part of the channel with respect to the gravitational force direction.

By the thermal cycle method in the present application example, the biotip can be held in the first disposition or in the second disposition, and in the first disposition, the first portion of the biotip can be heated. The first disposition is such that the first portion of the channel constituting the biotip is in the lowest part of the channel with respect to the gravitational force direction. The second disposition is such that the second portion, which is a different portion from the first portion relative to the moving direction of the reaction mixture, is in the lowest part of the channel with respect to the gravitational force direction. In other words, the reaction mixture is kept within the first portion in the first disposition and within the second portion in the second disposition due to the gravitational force. It is noted that the first portion is heated by the heating unit, and because the second portion is a different portion from the first portion relative to the moving direction of the reaction mixture, the temperatures of the first portion and the second portion differ. Therefore, enabling to keep the reaction mixture at a predetermined temperature depending on whether the biotip is held in the first disposition or in the second disposition realizes a thermal cycle method that enables to readily control a heating time period.

BRIEF DESCRIPTION OF DRAWINGS

FIG. 12A is a table showing results of the thermal cycle process according to the example 1.

FIG. 12B is a table showing results of the thermal cycle process according to the example 2.

DESCRIPTION OF EMBODIMENTS

A preferred embodiment of the invention will be described with reference to the drawings in the following order. Note that the following embodiment does not in any way limit the scope of the invention laid out in the claims. Note that all elements of the following embodiment should not necessarily be taken as essential requirements for the invention.

1. Embodiment 1-1. Configuration of a thermal cycler according to an embodiment of the invention 1-2. Thermal cycle method using the thermal cycler of the embodiment 2. Modified Examples 3. Examples Example 1. Shuttle PCR Example 2. One-Step RT-PCR

1. EMBODIMENT

Figure 1A:
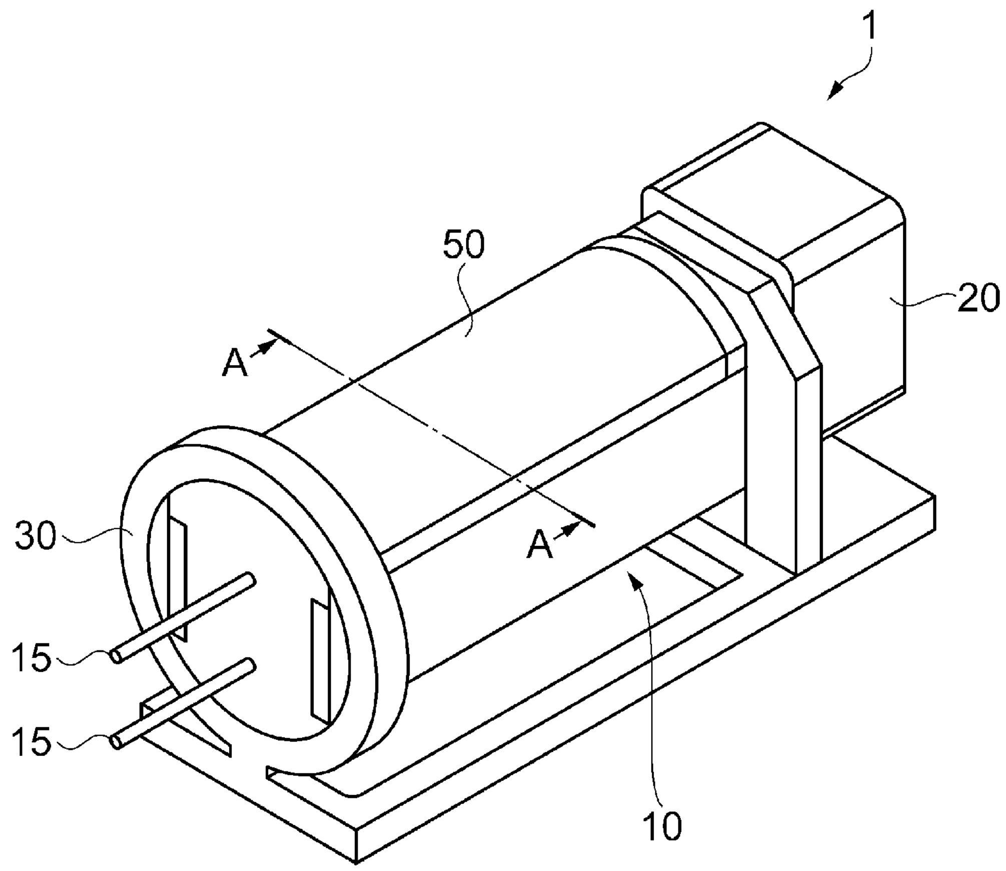
FIG. 1A is a perspective view of a thermal cycler according to an embodiment of the invention with its lid closed.
Figure 1B:
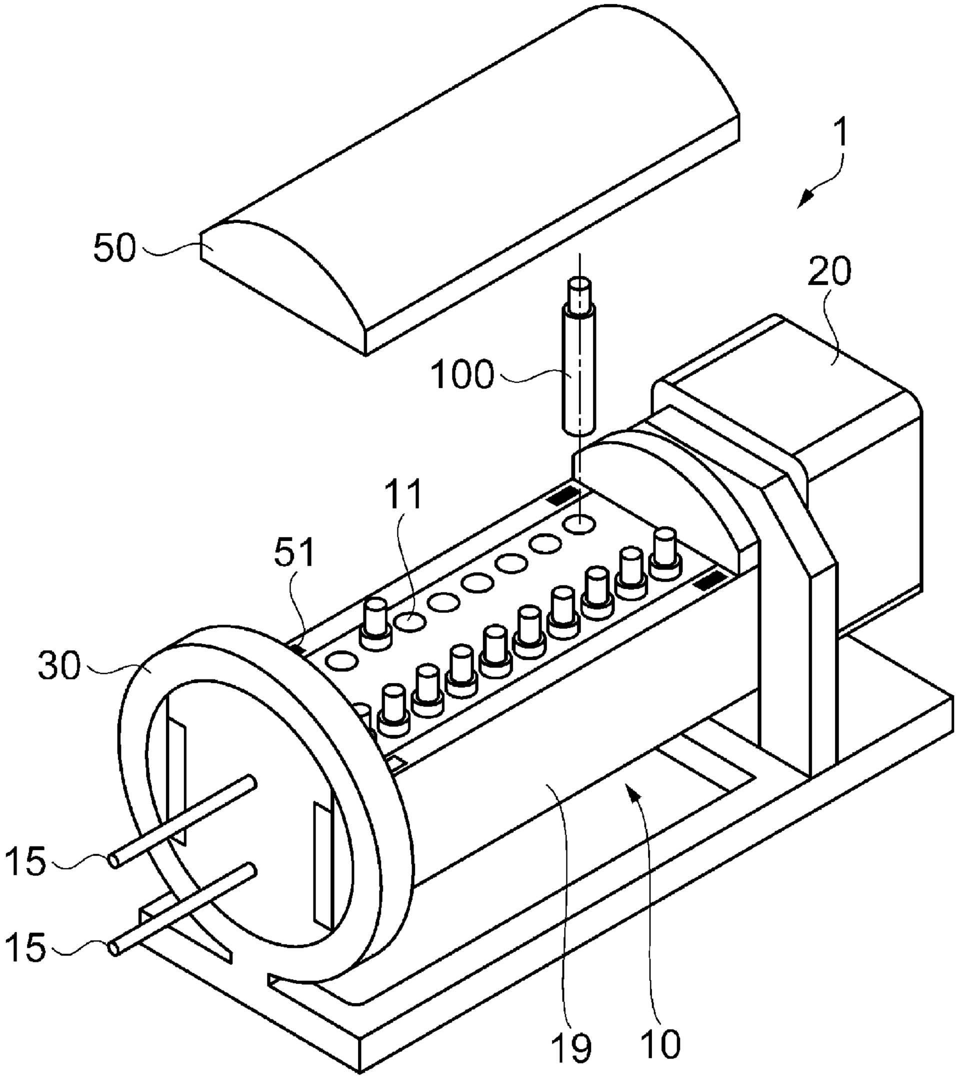
FIG. 1B is a perspective view of the thermal cycler according to the embodiment with its lid open.
Figure 2:
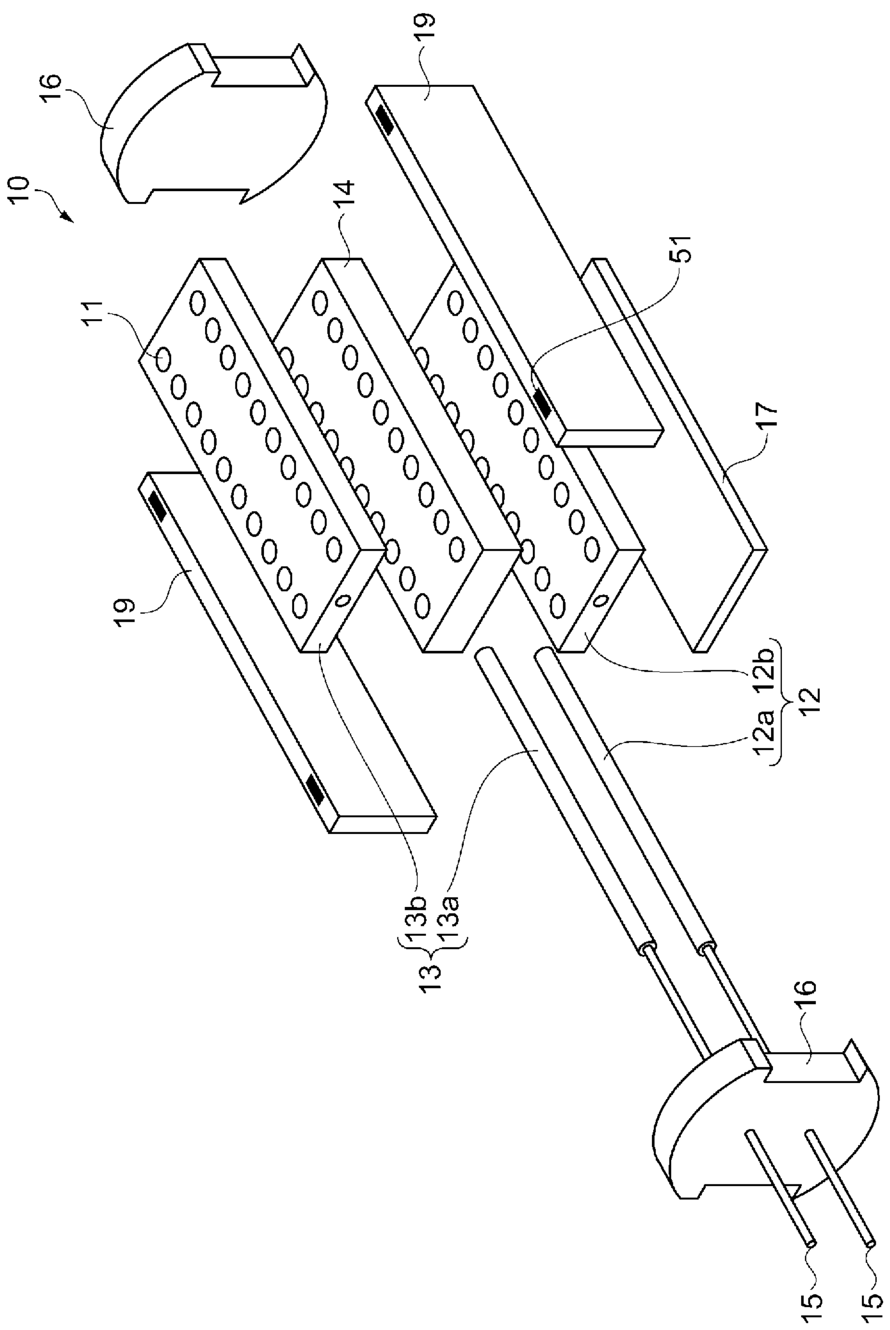
FIG. 2 is an exploded perspective view of a main unit of the thermal cycler according to the embodiment.
Figure 4A:
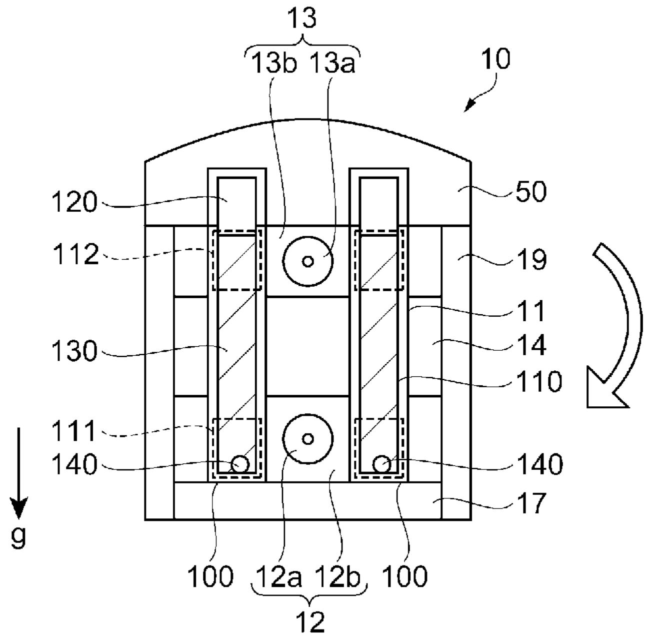
FIG. 4A is a cross sectional view illustrating a cross section of the main unit in a first disposition of the thermal cycler according to the embodiment along line A-A in FIG. 1A.

1-1. Configuration of a Thermal Cycler According to an Embodiment of the Invention FIG. 1A is a perspective view of a thermal cycler 1 according to an embodiment of the invention with its lid 50 closed, and FIG. 1B is a perspective view of the thermal cycler 1 with its lid 50 open, illustrating biotips 100 held in respective holders 11. FIG. 2 is an exploded perspective view of a main unit 10 of the thermal cycler 1 according to the embodiment. FIG. 4A is a cross sectional view illustrating a cross section of the main unit 10 of the thermal cycler 1 according to the embodiment along line A-A in FIG. 1A.

The thermal cycler 1 according to the embodiment, as shown in FIG. 1A, includes the main unit 10 and a driving unit 20. As shown in FIG. 2, the main unit 10 includes a holder 11, a first heating unit 12 (that corresponds to a heating unit) and a second heating unit 13. In between the first heating unit 12 and the second heating unit 13, a spacer 14 is provided. In the main unit 10 of the present embodiment, the first heating unit 12 is disposed in a closer side to a bottom plate 17, and the second heating unit 13 is disposed in a closer side to a lid 50. In the main unit 10 of the present embodiment, the first heating unit 12, the second heating unit 13, and the spacer 14 are fixed to flanges 16, the bottom plate 17 and locking plates 19.

The holder 11 has a structure that holds a biotip 100 described later. As shown in FIGS. 1B and 2, the holder 11 of the present embodiment has a slot structure into which the biotip 100 is inserted to be held therein. The biotip 100 will be inserted into an opening that penetrates through a first heating block **12*b* of the first heating unit 12 (the heating unit), the spacer 14, and a second heating block 13*b* of the second heating unit 13. The number of the holder 11 may be one or more. The main unit 10 has a total of 20 holders 11 in the example shown in FIG. 1**B.

Figure 4B:
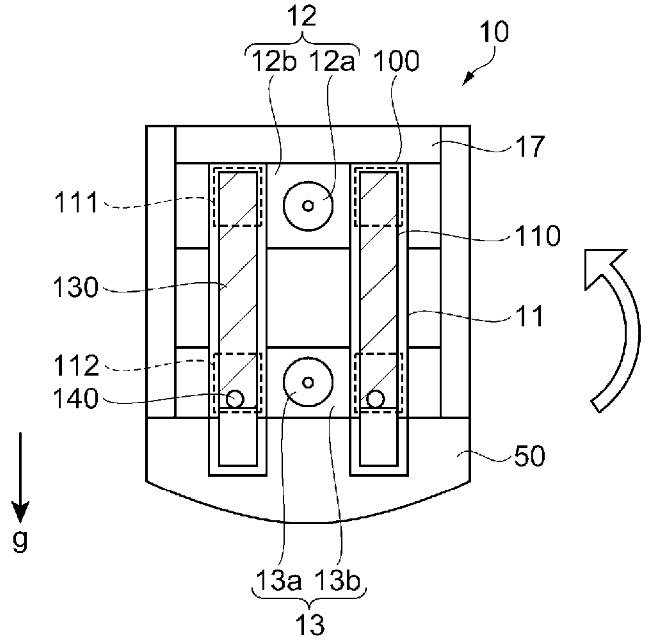
FIG. 4B is a cross sectional view illustrating a cross section of the main unit in a second disposition of the thermal cycler according to the embodiment along line A-A in FIG. 1A.

It is preferable that the thermal cycler 1 in the present embodiment include a structure that holds the biotip 100 at a predetermined position with respect to the first heating unit 12 and the second heating unit 13, so that the first heating unit 12 and the second heating unit 13 are able to heat predetermined portions of the biotip 100. More specifically, as shown in FIGS. 4A and 4B, a first portion 111 and a second portion 112 of a channel 110 constituting the biotip 100 are heated by the first heating unit 12 and the second heating unit 13, respectively, as described later. In the present embodiment, a structure that positions the biotip 100 is the bottom plate 17. As shown in FIG. 4A, inserting the biotip 100 to a position where the biotip 100 reaches the bottom plate 17 holds the biotip 100 at the predetermined position with respect to the first heating unit 12 and the second heating unit 13.

When the biotip 100 is in the holder 11, the first heating unit 12 heats the first portion 111 of the biotip 100, described later, to a first temperature. In FIG. 4A for example, the first heating unit 12 is disposed in a position in the main unit 10 so as to heat the first portion 111 of the biotip 100.

The first heating unit 12 may include a mechanism that generates heat and a part that conducts the generated heat to the biotip 100. In FIG. 2 for example, the first heating unit 12 includes a first heater **12*a* and a first heating block 12*b*. In the present embodiment, the first heater 12*a* is a cartridge heater that is connected to an external power source (not shown in the figures) via a conductor wire 15. The first heater 12*a*, inserted in the first heating block 12*b*, generates heat thereby heating up the first heating block 12*b*. The first heating block 12*b* is a part that conducts the heat generated by the first heater 12*a* to the biotip 100. In the present embodiment, an aluminum block is used for the first heating block 12*b***.

It is easy to control the temperature in cartridge heaters, and therefore a cartridge heater is used for the first heater **12*a* to readily stabilize the temperature of the first heating unit 12. Thus, more accurate application of thermal cycles is realized. Aluminum has a high thermal conductivity, and for that reason the first heating block 12*b* is made of aluminum to effectively heat the biotip 100. The first heating block 12*b* has only little unevenness of heat, and hence application of thermal cycles with higher accuracy is realized. Also, aluminum is easy to work with, and hence the first heating block 12*b*** may be molded with precision, improving accuracy in heating as a result. Thus, more accurate application of thermal cycles is realized.

It is preferable that the first heating unit 12 be in contact with the biotip 100 when the biotip 100 is in the holder 11. With such configuration, when the first heating unit 12 heats the biotip 100, the heat from the first heating unit 12 is conducted to the biotip 100 in a stable manner, thereby stabilizing the temperature of the biotip 100. If the holder 11 is formed as a part of the heating unit 12 as in the present embodiment, it is preferable that the holder 11 be in contact with the biotip 100. With such configuration, the heat from the first heating unit 12 is conducted to the biotip 100 in a stable manner, and hence the biotip 100 is effectively heated up.

When the biotip 100 is in the holder 11, the second heating unit 13 heats the second portion 112 of the biotip 100 to a second temperature different from the first temperature. In FIG. 4A for example, the second heating unit 13 is disposed in the main unit 10 so as to heat the second portion 112 of the biotip 100. As shown in FIG. 2, the second heating unit 13 includes a second heater 13*a* and a second heating block 13*b*. The second heating unit 13 has substantially the same functions as the first heating unit 12, except that the second heating unit 13 heats a different portion of the biotip 100 to a different temperature.

In the present embodiment, the temperatures of the first heating unit 12 and the second heating unit 13 are controlled by a temperature sensor and a control unit (both not shown in the figures) described later. It is preferable that the temperatures of the first heating unit 12 and the second heating unit 13 be set so as to heat the biotip 100 to desired temperatures. In the present embodiment, controlling the temperature of the first heating unit 12 to a first temperature and the second heating unit 13 to a second temperature enables to heat the first portion 111 of the biotip 100 to the first temperature and the second portion 112 of the biotip 100 to the second temperature. In the present embodiment, the temperature sensor is a thermocouple.

The driving unit 20 is a mechanism that drives the holder 11, the first heating unit 12, and the second heating unit 13. In the present embodiment, the driving unit 20 includes a motor and a driving shaft (both not shown in the figures). The driving shaft and the flange 16 of the main unit 10 are connected. The driving shaft in the present embodiment is provided perpendicular to the longitudinal direction of the holder 11. When the motor is in operation, the main unit 10 rotates about the driving shaft, which is used as the rotational axis.

The thermal cycler 1 of the present embodiment includes a control unit (not shown in the figures). The control unit controls at least one of the following parameters, all to be described later: the first temperature, the second temperature, a first period of time, a second period of time, and the number of thermal cycles. When the control unit controls the first period of time or the second period of time, the control unit controls an operation of the driving unit 20, thereby controlling a time period for which the holder 11, the first heating unit 12, and the second heating unit 13 are kept in a predetermined disposition. The control unit may be provided with a separate mechanism for each of the parameters to control, or may control all of the parameters integrally.

The control unit of the thermal cycler 1 of the present embodiment controls all the above-mentioned parameters electronically. Examples of the control unit in the present embodiment include a processor such as a CPU, a memory unit such as a ROM (Read Only Memory) and a RAM (Random Access Memory). In the memory unit, various programs, data, or the like are stored for controlling the above-mentioned parameters. The memory unit also has a work area that temporarily stores data-in-process of various processes, processing results, and the like.

In the main unit 10 in the present embodiment, as shown in the example in FIGS. 2 and 4A, the spacer 14 is provided in between the first heating unit 12 and the second heating unit 13. The spacer 14 in the present embodiment is a supporting part that supports the first heating unit 12 and/or the second heating unit 13. Disposing the spacer 14 enables to fix the distance between the first heating unit 12 and the second heating unit 13 more accurately. That is, positions of the first heating unit 12 and the second heating unit 13 with respect to the first portion 111 and the second portion 112, respectively, of the biotip 100, to be described later, are defined with more accuracy.

Material for the spacer 14 may be selected in accordance with needs, but it is preferable that it be a thermally insulating material. Such configuration helps decrease mutual effect between the heat of the first heating unit 12 and the heat of the second heating unit 13, thereby enabling to readily control the temperature of the first heating unit 12 and the temperature of the second heating unit 13. If a thermally insulating material is used for the spacer 14, it is preferable that the spacer 14 be disposed surrounding a portion of the biotip 100 between the first heating unit 12 and the second heating unit 13 when the biotip 100 is in the holder 11. Such configuration helps suppress heat release from the potion between the first heating unit 12 and the second heating unit 13, thereby enabling to further stabilize the temperatures of the biotip 100. The spacer 14 in the present embodiment is a thermally insulating material, and as shown in FIG. 4A, the holder 11 penetrates through the spacer 14. Such configuration helps prevent heat loss from the biotip 100 when the first heating unit 12 and the second heating unit 13 heat the biotip 100, thereby enabling to further stabilize the temperature of the first portion 111 and the temperature of the second portion 112.

The main unit 10 in the present embodiment includes the locking plates 19. The locking plates 19 are supporting parts that support the holder 11, the first heating unit 12, and the second heating unit 13. In FIGS. 1B and 2 for example, two locking plates 19 are encased by the flanges 16, and the first heating unit 12, the second heating unit 13, and the bottom plate 17 are locked in place. The locking plates 19 make the main unit 10 a more rigid structure, and thus the main unit 10 is barely prone to damage.

The thermal cycler 1 of the present embodiment includes the lid 50. In FIGS. 1A and 4A for example, the holder 11 is covered with the lid 50. Covering the holder 11 with the lid 50 helps, when the first heating unit 12 applies heat, prevent the heat in the main unit 10 from being released externally, thereby enabling to stabilize the temperature inside the main unit 10. The lid 50 may be locked in place with locking parts 51. In the present embodiment, the locking parts 51 are magnets. As shown in FIGS. 1B and 2 for example, magnets are disposed on the surface of the main unit 10 where the lid 50 comes in contact. Although not shown in FIGS. 1B and 2, the lid 50 also has magnets disposed on the places that come in contact with the magnets of the main unit 10, and when the lid 50 covers the holder 11, the lid 50 is locked in place to the main unit 10 by magnetic force. Such configuration helps prevent the lid 50 from moving or coming off when the driving unit 20 drives the main unit 10. This prevents temperature changes inside the thermal cycler 1 due to the lid 50 coming off, enabling more accurate thermal cycles to be applied to a reaction mixture 140, described later.

It is preferable that the main unit 10 be a highly airtight structure. If the main unit 10 is a highly airtight structure, the air inside the main unit 10 is barely let out, which helps stabilize the temperature inside the main unit 10. In the present embodiment, as shown in FIG. 2, the two flanges 16, the bottom plate 17, the two locking plates 19, and the lid 50 seal the interior space of the main unit 10.

It is preferable that the locking plates 19, the bottom plate 17, the lid 50, and the flanges 16 be formed with thermally insulating material. Such configuration helps prevent the heat in the main unit 10 from being released externally in a more reliable manner, thereby enabling to further stabilize the temperature inside the main unit 10.

1-2. Thermal Cycle Method Using the Thermal Cycler of the Embodiment

Figure 3:
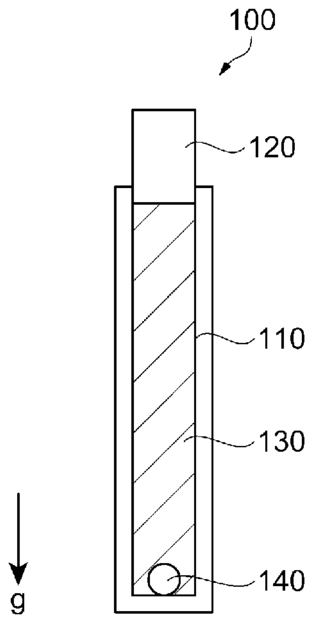
FIG. 3 is a cross sectional view of a biotip according to the embodiment.
Figure 5:
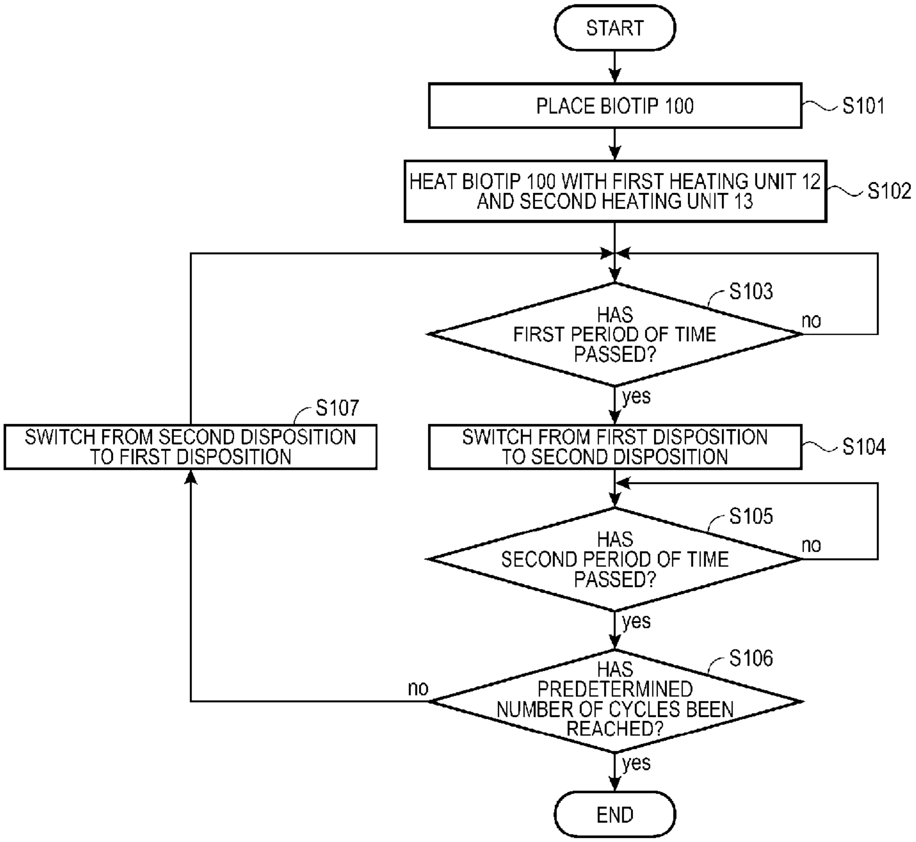
FIG. 5 is a flowchart showing a thermal cycle process using the thermal cycler of the embodiment.

FIG. 3 is a cross sectional view of the biotip 100 according to the embodiment. FIGS. 4A and 4B are cross sectional views illustrating a cross section of the thermal cycler 1 according to the embodiment along line A-A in FIG. 1A. FIGS. 4A and 4B show the thermal cycler 1 with the biotip 100 placed therein. FIG. 4A shows a first disposition, and FIG. 4B shows a second disposition. FIG. 5 is a flowchart showing a thermal cycle process using the thermal cycler 1 of the embodiment. Below, the biotip 100 according to the embodiment will be described first, and then a thermal cycle process using the biotip 100 with the thermal cycler 1 of the embodiment will be described.

As shown in FIG. 3, the biotip 100 according to the embodiment includes the channel 110 and a seal 120. The channel 110 is filled with a reaction mixture 140 and liquid 130 that has a smaller specific gravity than the reaction mixture 140 and is not immiscible with the reaction mixture 140 (hereinafter referred to as "liquid"), and sealed with the seal 120.

The channel 110 is formed in such a manner that the reaction mixture 140 moves in proximity to the internal facing wall sections. It is noted that the "internal facing wall sections" of the channel 110 indicate two sections of the wall of the channel 110 that are facing each other. Also it is noted that moving "in proximity to" indicates that the reaction mixture 140 and the wall of the channel 110 are close, and includes a case in which the reaction mixture 140 and the wall of the channel 110 come in contact. So when the reaction mixture 140 moves in proximity to the internal facing wall sections, that means that the reaction mixture 140 moves while keeping the distance close to both of the two sections of the wall of the channel 110 that are facing each other. In other words, the reaction mixture 140 moves alongside both of the internal facing wall sections. To put it another way, a distance between the two internal facing wall sections of the channel 110 is as much as the distance in which the reaction mixture 140 moves in proximity to those internal wall sections.

Forming the channel 110 of the biotip 100 described above enables to regulate a direction to which the reaction mixture 140 moves inside the channel 110, thereby enabling to define a path along which the reaction mixture 140 moves between the first portion 111 and the second portion 112, which is different from the first portion 111, of the channel 110 (described later) to a certain degree. Such configuration helps set the time required for the reaction mixture 140 to move between the first portion 111 and the second portion 112 within a certain range. Thus, it is preferable that a degree of "proximity" be as much as the time variations in the reaction mixture 140 moving between the first portion 111 and the second portion 112 do not affect the heating time periods to the reaction mixture 140 in both portions. That is to say, it is preferable that the time variations cause little effect on the reaction result. More specifically, the distance between the internal facing wall sections in the direction perpendicular to the moving directions of the reaction mixture 140 is preferably within a range in which less than two droplets of the reaction mixture 140 fit.

In FIG. 3 for example, the biotip 100 is cylinder-shaped, and the channel 110 is formed in the central axis direction (the vertical direction in FIG. 3). The shape of the channel 110 is tubular, and a cross section thereof perpendicular to the longitudinal direction of the channel 110, that is, a cross section at a given portion of the channel 110 in the direction perpendicular to the moving directions of the reaction mixture 140 (hereinafter referred to as a "cross section" of the channel 110), is round. Thus, in the biotip 100 in the present embodiment, the internal facing wall sections of the channel 110 are portions that include two points on the wall of the channel 110 constituting the diameter of a cross section of the channel 110. The reaction mixture 140 moves alongside the internal facing wall sections in the longitudinal direction of the channel 110.

The first portion 111 of the biotip 100 is a portion of the channel 110 that is heated by the first heating unit 12 to the first temperature. The second portion 112 is a portion of the channel 110 that is different from the first portion 111 and is heated by the second heating unit 13 to the second temperature. In the biotip 100 in the present embodiment, the first portion 111 is a portion that includes one end of the channel 110 in the longitudinal direction, and the second portion 112 is a portion that includes the other end of the channel 110 in the longitudinal direction. In FIGS. 4A and 4B for example, the portion in a dotted frame that includes an end on the side close to the seal 120 of the channel 110 is the second portion 112, and the portion in a dotted frame that includes an end on the side away from the seal 120 is the first portion 111.

The channel 110 has the liquid 130 and the reaction mixture 140 filled therein. The liquid 130 is not immiscible, or does not get mixed, with the reaction mixture 140 in nature, and hence, as shown in FIG. 3, the reaction mixture 140 is in the liquid 130 in the form of a droplet. The reaction mixture 140 has a larger specific gravity than the liquid 130, and hence is in the lowest portion of the channel 110 with respect to the gravitational force direction. Examples of the liquid 130 may include dimethyl silicone oil and paraffin oil. The reaction mixture 140 is liquid that contains constituents required for a reaction. When the reaction is a PCR, the reaction mixture 140 contains a target DNA sequence subjected to amplification in the PCR (target DNA), DNA polymerase required for amplifying the DNA, and a primer. For example, when a PCR is performed using oil as the liquid 130, it is preferable that the reaction mixture 140 be an aqueous solution that contains the above-mentioned constituents.

A thermal cycle process using the thermal cycler 1 of the embodiment will be described with reference to FIGS. 4A, 4B, and 5. In FIGS. 4A and 4B, a direction denoted by "g" with an arrow (the downward direction in the figures) is the gravitational force direction. It is noted that the present embodiment will describe a shuttle PCR (two-temperature PCR) as an example of the thermal cycle process. It is further noted that each of the steps described below is an example of the thermal cycle process. An order of the steps may be changed, two or more of the steps may be performed consecutively or in parallel, or another step may be added, as necessary.

In a shuttle PCR, a reaction mixture is processed under application of two stages (one high stage and one low stage) of temperature, and the process repeatedly continues on, thereby amplifying a nucleic acid sequence in the reaction mixture. In a treatment in the high stage of temperature, denaturation (a reaction in which a double-stranded DNA is denatured to become two single-strands of DNA) occurs. In a treatment in the low stage of temperature, annealing (a reaction in which a primer binds to a single-stranded DNA) and an elongation (a reaction in which the synthesis of the complementary strand of DNA initiated at the primer takes place) occur.

Generally in a shuttle PCR, the high stage of temperature is from 80 degrees Celsius to 100 degrees Celsius, and the low stage of temperature is from 50 degrees Celsius to 70 degrees Celsius. The treatments in each of the stages of temperature are conducted for predetermined periods of time, and generally the time period of the treatment in the high stage of temperature is set shorter than the time period of the treatment in the low stage of temperature. For example, the time period may be set ranging from 1 to 10 seconds for the treatment in the high stage of temperature, and the time period may be set ranging from 10 to 60 seconds for the treatment in the low stage of temperature. The time periods may be set longer depending on reaction conditions.

Note that it is preferable to consider the types of reagent or amount of the reaction mixture 140 to decide appropriate protocols before actually conducting the reaction because time periods, temperature, and the number of cycles (number of repetitions between the high and low stages of temperature) differ depending on the types and amount of reagent.

First, the biotip 100 in the present embodiment is placed in the holder 11 (S101). In the present embodiment, after the reaction mixture 140 is introduced in the channel 110 in which the liquid 130 is filled, the biotip 100 sealed with the seal 120 is placed in the holder 11. The reaction mixture 140 may be introduced with a micropipette, a dispensing device that utilizes an inkjet technology, or the like. When the biotip 100 is in the holder 11, the first heating unit 12 is positioned so as to contact the biotip 100 at a position including the first portion 111, and the second heating unit 13 is positioned so as to contact the biotip 100 at a position including the second portion 112. In the present embodiment, as shown in FIG. 4A, placing the biotip 100 in a position where the biotip 100 reaches the bottom plate 17 holds the biotip 100 at the predetermined position with respect to the first heating unit 12 and the second heating unit 13.

In the present embodiment, the disposition of the holder 11, the first heating unit 12, and the second heating unit 13 in S101 is a first disposition. As shown in FIG. 4A, the first disposition is such that the first portion 111 of the biotip 100 is in the lowest part of the channel 110 with respect to the gravitational force direction. Hence, when the holder 11, the first heating unit 12, and the second heating unit 13 are in the predetermined disposition, the first portion 111 is a portion of the channel 110 in the lowest part of the channel 110 with respect to the gravitational force direction. In the first disposition, the first portion 111 is positioned in the lowest part of the channel 110 with respect to the gravitational force direction, and thus the reaction mixture 140 having a larger specific gravity than the liquid 130 is in the first portion 111. In the present embodiment, after the biotip 100 is placed in the holder 11, the holder 11 is covered with the lid 50, and then the thermal cycler 1 is started. In the present embodiment, starting the thermal cycler 1 initiates the steps S102 and S103.

In S102, the first heating unit 12 and the second heating unit 13 heat the biotip 100. The first heating unit 12 and the second heating unit 13 heat different portions of the biotip 100 to different temperatures. In other words, the first heating unit 12 heats the first portion 111 to the first temperature, and the second heating unit 13 heats the second portion 112 to the second temperature. Such configuration forms in between the first portion 111 and the second portion 112 of the channel 110 a temperature gradient in which the temperature gradually changes between the first temperature and the second temperature. In the present embodiment, the first temperature is a relatively high temperature among the temperatures appropriate for the desired reaction in the thermal cycle process, and the second temperature is a relatively low temperature among the temperatures appropriate for the desired reaction in the thermal cycle process. Thus, in S102 of the present embodiment, the temperature gradually lowers from the first portion 111 toward the second portion 112, forming a temperature gradient. The thermal cycle process in the present embodiment is a shuttle PCR, and hence it is preferable that the first temperature be an appropriate temperature for denaturing a double-stranded DNA and the second temperature be appropriate for annealing and elongation.

In S102, the holder 11, the first heating unit 12, and the second heating unit 13 are in the first disposition, and hence, when the biotip 100 is heated in S102, the reaction mixture 140 is heated to the first temperature. Thus, in S102, the reaction of the reaction mixture 140 at the first temperature occurs.

In S103, a determination is made whether a first period of time has passed in the first disposition. In the present embodiment, the determination is made by the control unit (not illustrated). The first period of time is a time period for which the holder 11, the first heating unit 12, and the second heating unit 13 are kept in the first disposition. In the present embodiment, in a case where the placing step in S101 is followed by S103, in other words when S103 is performed for the first time, the determination of whether the first period of time has passed is made based on the time that has passed since the thermal cycler 1 was started. In the first disposition, the reaction mixture 140 is heated to the first temperature, and hence it is preferable that the first period of time be a time period for which the reaction mixture 140 is heated to the first temperature for the desired reaction. In the present embodiment, it is preferable that the first period of time be a time period required for denaturation of the double-stranded DNA.

When it is determined that the first period of time has passed (yes) in S103, the process proceeds to S104. When it is determined that the first period of time has not yet passed (no), then S103 is repeated.

In S104, the driving unit 20 drives the main unit 10 to switch the disposition of the holder 11, the first heating unit 12, and the second heating unit 13 from the first disposition to the second disposition. The second disposition is such that the second portion 112 is in the lowest part of the channel 110 with respect to the gravitational force direction. To put it in another way, the second portion 112 is in a portion in the lowest part of the channel 110 with respect to the gravitational force direction when the holder 11, the first heating unit 12, and the second heating unit 13 are in a predetermined disposition that is different from the first disposition.

In S104 in the present embodiment, the disposition of the holder 11, the first heating unit 12, and the second heating unit 13 is switched from the disposition of FIG. 4A to the disposition of FIG. 4B. In the thermal cycler 1 of the present embodiment, the control unit controls the driving unit 20 to rotate the main unit 10. Specifically the motor rotates the flanges 16 about the driving shaft, which is used as the rotational axis, thereby rotating the holder 11, the first heating unit 12, and the second heating unit 13 fixed to the flanges 16. The driving shaft has an axis perpendicular to the longitudinal direction of the holder 11, and hence when the motor operates to rotate the driving shaft, the holder 11, the first heating unit 12, and the second heating unit 13 are rotated. In FIG. 4A and FIG. 4B for example, the main unit 10 is rotated 180 degrees, thereby switching the disposition of the holder 11, the first heating unit 12, and the second heating unit 13 from the first disposition to the second disposition.

The positional relation in S104 between the first portion 111 and the second portion 112 with respect to the gravitational force direction is reverse from the first disposition. The reaction mixture 140 moves from the first portion 111 to the second portion 112 due to the gravitational force. When the holder 11, the first heating unit 12, and the second heating unit 13 have come to be in the second disposition, and the control unit stops the movement of the driving unit 20, the holder 11, the first heating unit 12, and the second heating unit 13 are held in the second disposition. When the holder 11, the first heating unit 12, and the second heating unit 13 have come to be in the second disposition, the process proceeds to S105.

In S105, a determination is made whether a second period of time has passed in the second disposition. The second period of time is a time period for which the holder 11, the first heating unit 12, and the second heating unit 13 are kept in the second disposition. In the present embodiment, the second portion 112 is heated to the second temperature in S102, and therefore the determination of whether the second period of time has passed is made based on the time that has passed since the holder 11, the first heating unit 12, and the second heating unit 13 came to be in the second disposition. In the second disposition, the reaction mixture 140 is in the second portion 112, and hence, the reaction mixture 140 is heated to the second temperature as long as the main unit 10 is kept in the second disposition. Thus, it is preferable that the second period of time be a time period for which the reaction mixture 140 is heated to the second temperature for the desired reaction. In the present embodiment, it is preferable that the second period of time be a time period required for annealing and elongation.

When it is determined that the second period of time has passed (yes) in S105, the process proceeds to S106. When it is determined that the second period of time has not yet passed (no), then S105 is repeated.

In S106, a determination is made whether the number of thermal cycles has reached a predetermined number of cycles. Specifically, it is determined whether the steps S103 through S105 have been completed a predetermined number of times. In the present embodiment, the number of times both steps S103 and S105 have been determined "yes" is determined to be the number of times the steps S103 through S105 have been completed. Every time the steps S103 through S105 are performed, the reaction mixture 140 gets treated with one thermal cycle. Hence, the number of times the steps S103 through S105 have been completed may be considered to represent the number of thermal cycles. It is thus determinable in S106 whether thermal cycles have been applied a required number of times for the desired reaction.

When it is determined that the predetermined number of thermal cycles has been applied (yes) in S106, the process ends (END). When it is determined that the number of thermal cycles has not yet been applied (no), the process proceeds to S107.

In S107, the disposition of the holder 11, the first heating unit 12, and the second heating unit 13 is switched from the second disposition to the first disposition. The driving unit 20 drives the main unit 10 to dispose the holder 11, the first heating unit 12, and the second heating unit 13 in the first disposition. When the holder 11, the first heating unit 12, and the second heating unit 13 have come to be in the first disposition, the process proceeds to S103.

When S103 is performed following S107, or in S103 performed for the second or any subsequent time, a determination of whether the first period of time has passed is made based on the time that has passed since the holder 11, the first heating unit 12, and the second heating unit 13 came to be in the first disposition.

It is preferable that a direction in which the driving unit 20 rotates the holder 11, the first heating unit 12, and the second heating unit 13 in S107 be opposite from the direction of the rotation in S104. Such configuration enables to undo the kinked wiring occurred to the wiring such as conductor wires 15 as a result of the rotation and suppresses wear-out of the wiring. It is preferable that the direction of the rotation be reversed every movement of the driving unit 20. Such configuration enables to reduce the possibilities of the wiring getting kinked compared to a case where rotations are consecutively performed several times in a single direction.

1-3. Advantages of the Thermal Cycler and the Thermal Cycle Process of the Embodiment The thermal cycler and the thermal cycle method according to the present embodiment can bring the following advantages.

(1) The thermal cycler 1 of the present embodiment includes the first heating unit 12 and the second heating unit 13, and hence the reaction mixture 140 is heated to the first temperature in the first disposition and to the second temperature in the second disposition. The driving unit 20 switches the disposition of the holder 11, the first heating unit 12, and the second heating unit 13 to move the reaction mixture 140 in accordance with the gravitational force, thereby switching the temperatures of the heat applied. A time period for which the biotip 100 is held in the first disposition or in the second disposition corresponds to a time period of heating the reaction mixture 140. Thus, the time periods of heating the reaction mixture 140 are readily controllable in the thermal cycle process.

(2) The thermal cycler 1 of the present embodiment switches the disposition of the holder 11, the first heating unit 12, and the second heating unit 13 from the first disposition to the second disposition when the first period of time has passed, and from the second disposition to the first disposition when the second period of time has passed. Such configuration allows for the reaction mixture 140 to be heated at the first temperature for the first period of time, and at the second temperature for the second period of time, thus enabling to control the heating time periods of the reaction mixture 140 more accurately. This enables more accurate thermal cycles to be applied to the reaction mixture 140.

2. MODIFIED EXAMPLES

Figure 6A:
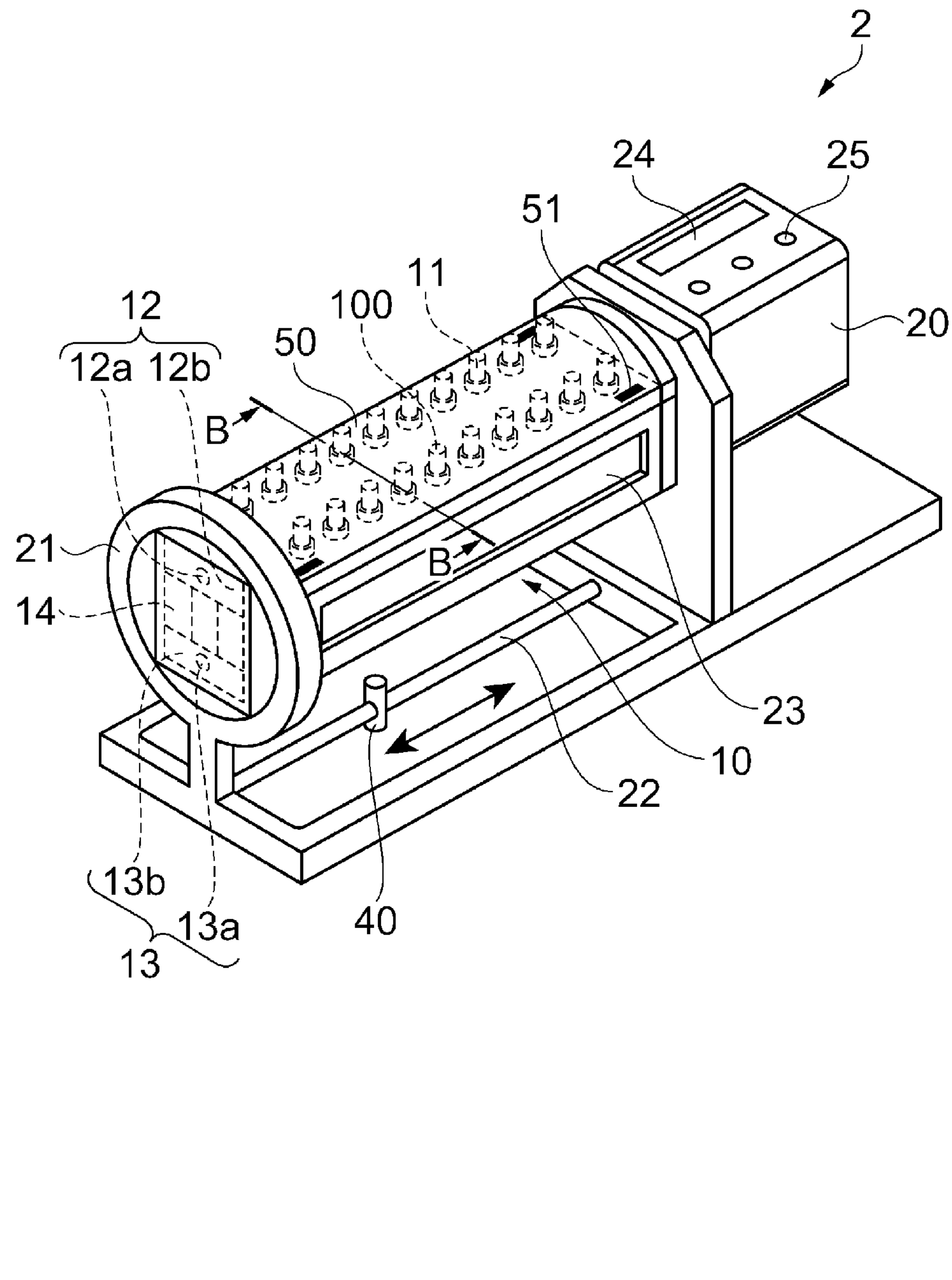
FIG. 6A is a perspective view of a thermal cycler in a modified example with its lid closed.
Figure 6B:
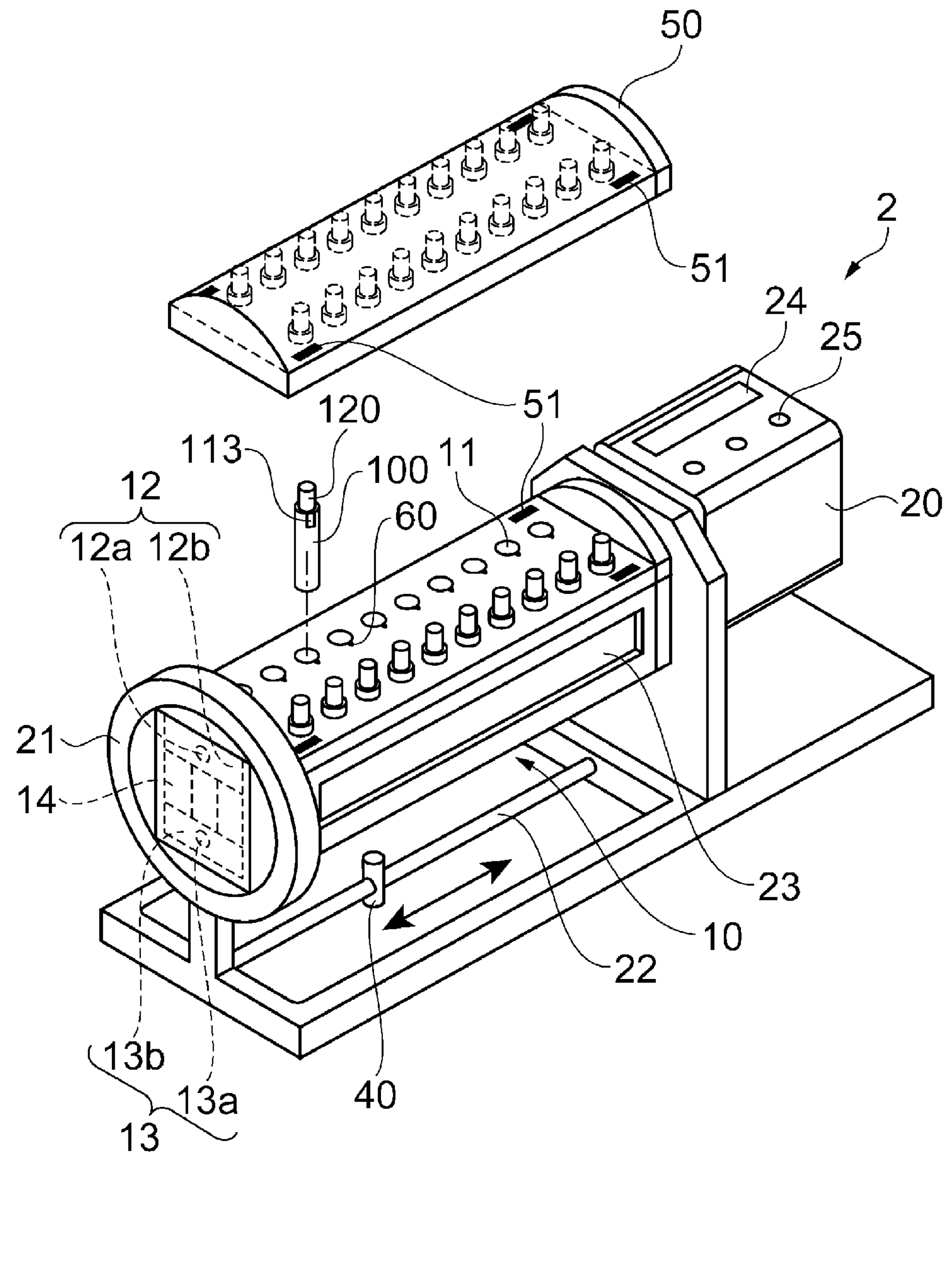
FIG. 6B is a perspective view of the thermal cycler in the modified example with its lid open.
Figure 7:
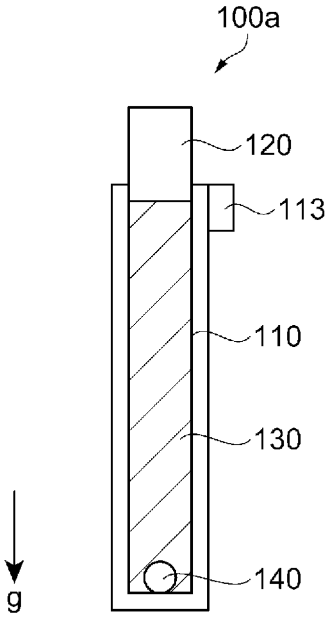
FIG. 7 is a cross sectional view of a biotip according to the modified example.
Figure 8:
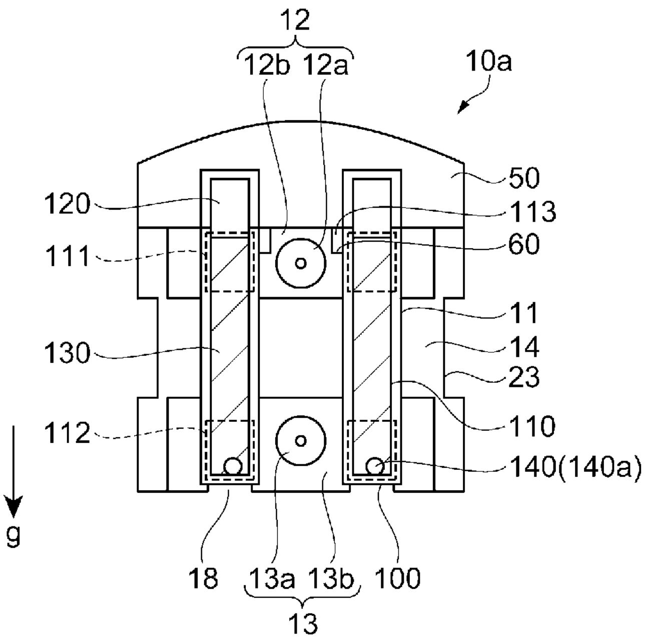
FIG. 8 is a cross sectional view illustrating a cross section of a main unit of the thermal cycler according to the modified example along line B-B in FIG. 6A.

Modified examples will be described based on the embodiment. FIG. 6A is a perspective view of a thermal cycler 2 according to the modified examples with its lid 50 closed, and FIG. 6B is a perspective view of a thermal cycler 2 according to the modified examples with its lid 50 open. FIG. 7 is a cross sectional view of a biotip 100*a* according to the modified example 4. FIG. 8 is a cross sectional view illustrating a cross section of a main unit 10*a* of the thermal cycler 2 according to the modified examples along line B-B in FIG. 6A. The modified examples given below may be combined as long as the configuration features are consistent with each other. The thermal cycler 2 shown in FIGS. 6A, 6B, and 8 is an example of a combination of the modified examples 1, 4, 16 and 17. Those modified examples will be described with reference to FIGS. 6A, 6B and FIG. 8. Elements that are not common to the elements in the embodiment will be described in detail, and the elements with the same or similar configuration as the embodiment already described above are referenced by the same numerals, and a detailed description thereof is omitted.

Modified Example 1

The embodiment presents an example of the thermal cycler 1 that does not include a detector, however, as shown in FIGS. 6A and 6B, the thermal cycler 2 of the modified examples may include a fluorescence detector 40. Such configuration enables the thermal cycler 2 to be used for the purpose of real-time PCR in which fluorescence detection is utilized. As long as the detections are conducted properly, a single or multiple fluorescence detector(s) 40 may be used. In this modified example, a single fluorescence detector 40 moves along a slide 22 to conduct fluorescence detection. It is preferable for conducting fluorescence detection that a measurement window 18 (refer to FIG. 8) be provided closer to the second heating unit 13 than the first heating unit 12 on the main unit 10*a*. Such configuration reduces parts in between the fluorescence detector 40 and the reaction mixture 140, and hence enables more accurate fluorescence measurement.

In this modified example, the thermal cycler 2 shown in FIGS. 6A, 6B, and 8 has the first heating unit 12 disposed in a closer side to the lid 50 and the second heating unit 13 disposed farther away from the lid 50. That is, the positional relation of the first heating unit 12, the second heating unit 13, and other parts included in the main unit 10 is different from that of the thermal cycler 1. Other than the positional relation, the first heating unit 12 and the second heating unit 13 function substantially the same way in the embodiment. In this modified example, as shown in FIG. 8, the second heating unit 13 is provided with the measurement window 18. Such configuration enables appropriate fluorescence measurement in a real-time PCR in which fluorescence is measured on the lower temperature side (the temperature at which annealing and elongation take place). If fluorescence is to be measured from the side of or near the lid 50, it is preferable that the seal 120 or the lid 50 be designed so as not to affect the measurement.

Modified Example 2

In the embodiment, the first temperature and the second temperature are constant from the beginning to the end of the thermal cycle process, however, either or both of the first temperature and the second temperature may be changed during the process. The first temperature and the second temperature may be changed by the control unit. Switching the disposition of the first heating unit 12 and the holder 11 thereby moving the reaction mixture 140 enables the reaction mixture 140 to be heated to a temperature that has been changed. Thus, it enables to conduct reactions that require two or more combinations of temperature, for example a reverse transcription PCR (also referred to as RT-PCR, the reaction of which will be briefly described in an example), without increasing the number of heating units or complicating the structure of the cycler.

Modified Example 3

The embodiment presents an example of the holder 11 having a slot structure, however, the holder 11 may be of any structure that is able to hold the biotip 100. For example, a structure having a hollow shaped alike the biotip 100 into which the biotip 100 is fit, or a structure that holds the biotip 100 by sandwiching therewith may be employed.

Modified Example 4

The embodiment presents an example of the structure in which the bottom plate 17 positions the biotip 100, however, a positioning structure may be of anything that is able to position the biotip 100 at a desired position. A positioning structure may be a structure provided in the thermal cycler 1, in the biotip 100, or in the both. For example, screws, insertable rods, a biotip 100 having a projecting part, or a structure that makes the holder 11 and the biotip 100 fit to each other may be employed. When using a screw or rod, a length of the screw itself or a length of a part that is screwed in, or a position of the rod where inserted may be adjusted to be able to change the position of the biotip 100 depending on a reaction condition of thermal cycles or the size of the biotip 100.

The structure that makes the biotip 100 and the holder 11 fit to each other, as shown in FIGS. 6A, 6B, 7, and 8 for example, may be such that the projecting part 113 provided on the biotip 100 fits with a recess 60 provided on the holder 11. Such configuration enables to keep a certain orientation of the biotip 100 with respect to the first heating unit 12 and/or the second heating unit 13. Thus, it suppresses orientational changes of the biotip 100 in middle of a thermal cycle, enabling to control heating more precisely. Thus, it enables to apply more accurate thermal cycles to the reaction mixture.

Modified Example 5

The embodiment presents an example of the first heating unit 12 and the second heating unit 13 being cartridge heaters, however, the first heating unit 12 may be of any heating mechanism that is able to heat the first portion 111 to the first temperature. The second heating unit 13 may be of any heating mechanism that is able to heat the second portion 112 to the second temperature. Examples that may be used for the first heating unit 12 and the second heating unit 13 include a carbon heater, sheet heater, IH heater (electromagnetic induction heater), Peltier element, heated liquid and heated gas. It is noted that a different type of heating mechanisms may be employed for the first heating unit 12 and the second heating unit 13.

Modified Example 6

The embodiment presents an example of the biotip 100 being heated by the first heating unit 12 and the second heating unit 13, however, a cooling unit that cools the second portion 112 may be provided in place of the second heating unit 13. For example, a Peltier element may be employed for the cooling unit. Such configuration enables to form a desired temperature gradient in the channel 110 even when the temperature of the second portion 112 does not get lowered easily due to the heat in the first portion 111 of the biotip 100. Or, for example, a thermal cycle of heating and cooling may be repeatedly applied to the reaction mixture 140.

Modified Example 7

The embodiment represents an example of the first heating block 12*b* and the second heating block 13*b* made of aluminum, however, material used for the heating blocks may be selected based on conditions including thermal conductivity, heat retaining characteristics, material workability, and the like. For example, copper alloy may be used alone or in combination with other kinds of material. Material used for the first heating block 12*b* and the second heating block 13*b* may differ.

Modified Example 8

As described in the embodiment as an example, when the holder 11 is formed as a part of the first heating unit 12, a contact mechanism that brings the holder 11 and the biotip 100 in contact may be employed. It is sufficient for the contact mechanism to bring at least a part of the biotip 100 in contact with the holder 11. For example, a spring provided on the main unit 10 or the lid 50 may push the biotip 100 against a surface of the wall of the holder 11. With such configuration, the heat from the first heating unit 12 is conducted to the biotip 100 in a more stable manner, further stabilizing the temperature of the biotip 100.

Modified Example 9

The embodiment presents an example of the first heating unit 12 and the second heating unit 13 being controlled to apply the temperatures that are substantially equal to the temperatures to which the respective portions of the biotip 100 are to be heated. However, the temperature control of the first heating unit 12 and the second heating unit 13 is not limited thereto. The temperatures of the first heating unit 12 and the second heating unit 13 may be controlled so as to heat the first portion 111 and the second portion 112 of the biotip 100 to the desired temperatures, respectively. For example, considering the size or the material of the biotip 100 enables to bring the temperatures of the first portion 111 and the second portion 112 to the desired temperatures in a more accurate manner.

Modified Example 10

The embodiment presents an example of the driving unit 20 being a motor, however, the driving unit 20 may be of any mechanism as long as the driving unit 20 is able to drive the holder 11, the first heating unit 12, and the second heating unit 13. If a driving mechanism capable of rotating the holder 11, the first heating unit 12, and the second heating unit 13 is used for the driving unit 20, it is preferable that the rotating speed of the driving unit 20 be controllable to a degree not to disturb the temperature gradient of the liquid 130 due to a centrifugal force. It is also preferable for the driving mechanism to be able to reverse its rotating direction so as to undo the kinked wiring. Examples for such driving mechanism include a mechanism with a turning handle or spiral spring.

Modified Example 11

The embodiment presents an example of the holder 11 being a part of the first heating unit 12, however, the holder 11 and the first heating unit 12 may be independent parts as long as the positional relation of the both does not change when the driving unit 20 is in operation. If the holder 11 and the first heating unit 12 are independent parts, then it is preferable that both parts be fixed to each other directly or with another part. The holder 11 and the first heating unit 12 may be driven by a single driving mechanism or by independent driving mechanisms, but it is preferable for the driving mechanism(s) to keep the positional relation of the holder 11 and the first heating unit 12 constant. Such configuration enables to keep the positional relation of the holder 11 and the first heating unit 12 constant when the driving unit 20 is in operation, and to heat the predetermined portions of the biotip 100 to the predetermined temperatures. It is noted that, if the holder 11, the first heating unit 12, and the second heating unit 13 are driven by separate driving mechanisms, then the separate driving mechanisms as a whole is considered a driving unit 20.

Modified Example 12

The embodiment presents an example of the temperature sensor being thermocouple, however, a resistance temperature detector or thermistor, for example, may also be used.

Modified Example 13

The embodiment presents an example of the locking parts 51 being magnets, however, the locking parts 51 may be any part capable of keeping the lid 50 and the main unit 10 locked in place. Examples of such may include hinges or catch clips.

Modified Example 14

In the embodiment, the axial direction of the driving shaft is perpendicular to the longitudinal direction of the holder 11, however, the axial direction may be optional as long as the disposition of the holder 11, the first heating unit 12, and the second heating unit 13 is switchable between the first disposition and the second disposition. In a case where the driving unit 20 is a driving mechanism that drives to rotate the holder 11, the first heating unit 12, and the second heating unit 13, the rotational axis is set to be a non-parallel line relative to the longitudinal direction of the holder 11, thereby making the disposition of the holder 11, the first heating unit 12, and the second heating unit 13 switchable.

Modified Example 15

The embodiment represents an example of the control unit controlling electronically, however, a control unit that controls the first period of time or the second period of time (time control unit) may be any controller capable of controlling the first period of time or the second period of time. That is, any controller that is able to control the start or stop of the movement of the driving unit 20 may be used. A control unit that controls the number of thermal cycles (cycle repetition control unit) may be any controller capable of controlling the number of cycles. For the time control unit or the cycle repetition control unit, for example, physical mechanisms, electronically controlled mechanisms, or a combination of the both may be employed.

Modified Example 16

The thermal cycler, as shown in FIGS. 6A and 6B, may include a configuration unit 25. The configuration unit 25 is a UI (User Interface) that sets conditions for a thermal cycle. Operation on the configuration unit 25 enables to configure at least one of the following parameters: the first temperature, the second temperature, the first period of time, the second period of time, and the number of thermal cycles. The configuration unit 25 is coupled to the control unit either mechanically or electronically, and the parameters configured in the configuration unit 25 are reflected to the control performed by the control unit. Such configuration enables to change conditions for the reaction and hence enabling to apply desired thermal cycles to the reaction mixture 140. The configuration unit 25 may configure any of the above-mentioned parameters separately, or may configure a set of required parameters, for example, a set of parameters corresponding to a set of reaction conditions selected among sets of pre-registered reaction conditions. In FIGS. 6A and 6B for example, the configuration unit 25 has buttons. Pressing a button provided for each parameter may enable to configure the reaction condition.

Modified Example 17

The thermal cycler, as shown in FIGS. 6A and 6B, may include a display 24. The display 24 is a displaying device, displaying various kinds of information regarding the thermal cycler. The display 24 may display the conditions configured in the configuration unit 25, or the current time or temperature in the middle of the thermal cycle process. For example, the display 24 may display the conditions according to the parameters having been configured, or in the middle of the thermal cycle process, the display 24 may display the temperature measured by the temperature sensor, the time as it passes while the first disposition or the second disposition is being kept, and the number of thermal cycles that have been applied. The display 24 may display a message when the thermal cycle process has ended or when a trouble has occurred to the cycler. The display 24 may also make vocal notifications. Displaying or making vocal notifications helps the user become aware of the progress during the thermal cycle process or the end thereof.

Modified Example 18

The embodiment represents an example of the biotip 100 having the channel 110 with a circular-shaped cross section, however, the channel 110 may be shaped otherwise as long as the reaction mixture 140 is able to move in proximity to internal facing wall sections. In other words, the channel 110 may be shaped such that the time variations that occur as the reaction mixture 140 moves between the first portion 111 and the second portion 112 will cause little effect on heating time periods of the reaction mixture 140 in both of the portions. It is noted that, if the biotip 100 has a channel 110 having a polygonal-shaped cross section, the "internal facing wall sections" are internal facing wall sections of the channel presumably having a channel with a circular cross section inside the channel 110. In other words, the channel 110 may be formed such that the reaction mixture 140 moves in proximity to the internal facing wall sections of an imaginary channel with a circular cross section internally in contact with the channel 110. Such configuration, when a cross section of the channel 110 is polygonal, enables to define a path along which the reaction mixture 140 moves between the first portion 111 and the second portion 112 to a certain degree. Thus, the time required for the reaction mixture 140 to move between the first portion 111 and the second portion 112 may be set within a certain range.

Modified Example 19

In the embodiment, the liquid 130 is liquid having a smaller specific gravity than the reaction mixture 140, however, the liquid 130 may be any type of liquid that is not immiscible with the reaction mixture 140 and has a different specific gravity from the reaction mixture 140. For example, liquid that is not immiscible with the reaction mixture 140 and has a larger specific gravity than the reaction mixture 140 may be used. If the liquid 130 has a larger specific gravity than the reaction mixture 140, the reaction mixture 140 will be in the uppermost part of the channel 110 with respect to the gravitational force direction.

Modified Example 20

In the embodiment, the rotational direction in S104 is a reverse of the rotational direction in S107, however, rotations may be made multiple times in one direction and then to the reverse direction for the same multiple times. Such configuration enables to undo the kinked wiring occurred to the wiring, thereby suppressing wear-out of the wiring compared to a case where no rotation in the reverse direction is made.

Modified Example 21

The thermal cycler 1 of the embodiment includes the first heating unit 12 and the second heating unit 13, however, the second heating unit 13 may be absent. In other words, the first heating unit 12 may be the only heating unit. Such configuration enables to reduce the number of parts used, thereby reducing the manufacturing cost.

In this modified example, the first heating unit 12 heats the first portion 111 of the biotip 100, thereby causing to form in the biotip 100 a temperature gradient in which the temperature gradually lowers as the distance from the first portion 111 increases. The second portion 112 is a different portion from the first portion 111, and hence is kept to a second temperature that is lower than that of the first portion 111. In this modified example, the second temperature is controllable based on, for example, design of the biotip 100, characteristics of the liquid 130, temperature setting of the first heating unit 12, or the like.

In this modified example, the driving unit 20 switches the disposition of the holder 11 and the first heating unit 12 between the first disposition and the second disposition, thereby moving the reaction mixture 140 between the first portion 111 and the second portion 112. The first portion 111 and the second portion 112 are held at different temperatures, and hence thermal cycles are applied to the reaction mixture 140.

If the second heating unit 13 is absent, the spacer 14 supports the first heating unit 12. Such configuration enables to position the first heating unit 12 relative to the main unit 10 more accurately, whereby the first portion 111 is heated in a more accurate manner. If a thermally insulating material is used for the spacer 14, disposing the spacer 14 in such a manner that it surrounds the biotip 100 in the portion other than the portion heated by the first heating unit 12 enables to stabilize the temperatures of the first portion 111 and the second portion 112.

In this modified example, the thermal cycler may include a mechanism that keeps the temperature of the main unit 10 constant. Such configuration enables to further stabilize the temperature in the second portion 112 of the biotip 100, enabling to apply more accurate thermal cycles to the reaction mixture 140. For example, a constant temperature bath may be employed for the mechanism to keep the main unit 10 at a constant temperature.

Modified Example 22

The embodiment presents an example of the thermal cycler 1 having the lid 50, however, the lid 50 may be absent. Such configuration enables to reduce the number of parts used, thereby reducing the manufacturing cost.

Modified Example 23

The embodiment presents an example of the thermal cycler 1 having the spacer 14, however, the spacer 14 may be absent.

Such configuration enables to reduce the number of parts used, thereby reducing the manufacturing cost.

Modified Example 24

The embodiment presents an example of the thermal cycler 1 having the bottom plate 17, however, as shown in FIG. 8, the bottom plate 17 may be absent. Such configuration enables to reduce the number of parts used, thereby reducing the manufacturing cost.

Modified Example 25

The embodiment presents an example of the thermal cycler 1 having the locking plates 19, however, the locking plates 19 may be absent. Such configuration enables to reduce the number of parts used, thereby reducing the manufacturing cost.

Modified Example 26

The embodiment presents an example of the spacer 14 and locking plates 19 are separate parts, however, as shown in FIG. 8, the spacer 14 and the locking plates 19 may be fabricated in unity. Moreover, the bottom plate 17 and the spacer 14, or the bottom plate 17 and the locking plates 19, may be fabricated in unity.

Modified Example 27

The spacer 14 and the locking plates 19 may be transparent. With such configuration, when a transparent biotip 100 is used for the thermal cycle process, the movement of the reaction mixture 140 is made observable from the external. Hence, whether the thermal cycle process is performed properly may be confirmed visually. It is noted that, when such transparent parts are used for the thermal cycler 1 to conduct the thermal cycle process, the parts may be transparent to a sufficient degree to make the movement of the reaction mixture 140 visually observable.

Modified Example 28

In order to observe the inside of the thermal cycler 1, the thermal cycler 1 may include any of the following combinations: the transparent spacer 14 and no locking plates 19; the transparent locking plates 19 and no spacer 14; or no spacer 14 and no locking plates 19. The fewer the parts in between an observer and the biotip 100 subjected to the observation, the less influence of refraction of light due to the parts. Hence such configuration makes it easier to observe the inside. Moreover, having fewer parts helps reducing the manufacturing cost.

Modified Example 29

In order to observe the inside of the thermal cycler 1, as shown in FIGS. 6A, 6B and 8, the main unit 10*a* may include an observation window 23. The observation window 23 may be, for example, an opening or a slit formed on the spacer 14 and/or on at least one of the locking plates 19. In FIG. 8 for example, the observation window 23 is a recess provided on the transparent spacer 14 fabricated in unity with the locking plates 19. With the observation window 23, thickness of the part between the observer and the biotip 100 subjected to observation is lessened, and hence making it easier to observe the inside.

Modified Example 30

The embodiment presents an example of the first heating unit 12 disposed in the closer side to the bottom plate 17 of the main unit 10, and of the second heating unit 13 disposed in the side closer to the lid 50, however, as shown in FIG. 8, the first heating unit 12 may be disposed in the closer side to the lid 50. If the first heating unit 12 is disposed in the closer side to the lid 50, then its disposition of the holder 11, the first heating unit 12, and the second heating unit 13 is in the second disposition when the biotip 100 is in the holder in S101 of the embodiment. In other words, the second portion 112 is in the lowest part of the channel 110 with respect to the gravitational force direction. Thus, when the thermal cycler 2 of this modified example is applied to the thermal cycle process of the embodiment, the disposition will be switched to the first disposition after the biotip 100 is placed in the holder 11. Specifically, S107 is performed following S101 before S102 and S103 are performed.

Modified Example 31

The embodiment presents an example in which the step of the first heating unit 12 and the second heating unit 13 heating the biotip 100 (S102) and the step of determining whether the first period of time has passed (S103) are performed after the biotip 100 is placed in the holder 11 (S101), however, the timing at which S102 is performed is not limited thereto. As long as the first portion 111 is heated to the first temperature before the clocking starts in S103, S102 may be performed at any timing. The timing for performing S102 is determined accounting for sizes of or material used for the biotip 100, a required time period for heating the first heating block 12*b*, and etc. For example, S102 may be performed at any timing of the following: prior to S101, simultaneously with S101, or after S101 but prior to S103.

Modified Example 32

The embodiment presents an example of the control unit controlling the first temperature, the second temperature, the first period of time, the second period of time and the number of thermal cycles and operation of the driving unit 20, however, the user may control one or more of the above. When the user controls the first temperature or the second temperature, the display 24 may display the temperature measured by the temperature sensor, and the user may operate the configuration unit 25 to adjust the temperature, for example. When the user controls the number of thermal cycles, the user stops the thermal cycler 1 when the predetermined number has been reached. The user may count the number of cycles, or the thermal cycler 1 may count the number of cycles and display the count on the display 24.

When the user controls the first period of time and/or the second period of time, the user may determine whether the predetermined time period has passed and make the thermal cycler 2 switch the disposition of the holder 11, the first heating unit 12, and the second heating unit 13. In other words, the user performs at least in part of S103 and S105, and of S104 and S107 in FIG. 5. A timer that is not coupled to the thermal cycler 2 may be used for keeping the time, or the thermal cycler 2 may display time on the display 24 as the time passes. Switching the disposition may be performed by operating the configuration unit 25 (UI) or performed manually using a handle provided on the driving unit 20.

Modified Example 33

The embodiment presents an example in which the rotational angle is 180 degrees when the driving unit 20 rotates to switch the disposition of the holder 11, the first heating unit 12, and the second heating unit 13, however, the rotational angle may be within a range that vertically changes the positional relation of the first portion 111 and the second portion 112 relative to the gravitational force direction. For example, if the rotational angle is smaller than 180 degrees, then the reaction mixture 140 moves slower. Thus, adjusting the rotational angle enables to adjust the time it takes for the reaction mixture 140 to move between the first temperature and the second temperature. In other words, it enables to adjust the time it takes for the temperature of the reaction mixture 140 to change between the first temperature and the second temperature.

3. EXAMPLES

The invention is further described using specific examples below, however, the scope of the invention is not limited to the description given in the examples.

Example 1

Shuttle PCR

Figure 9:
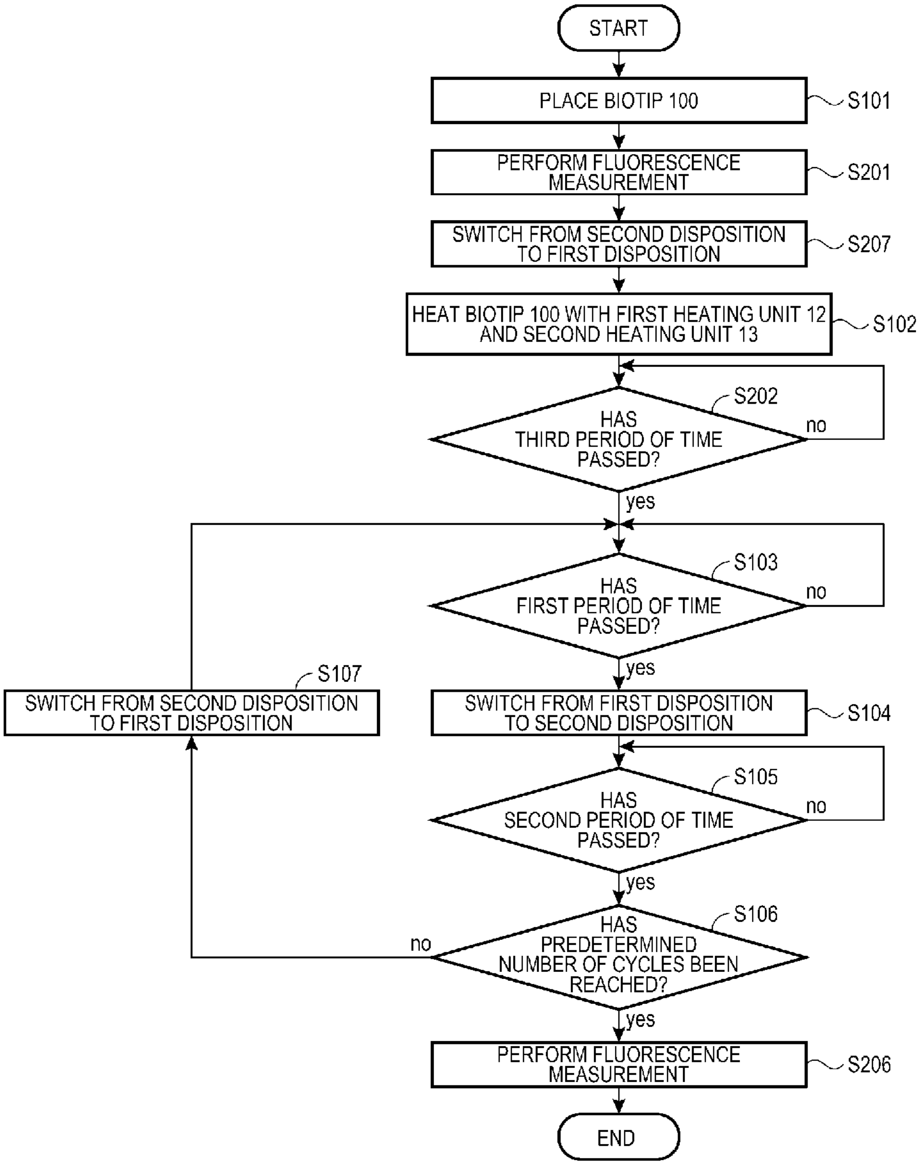
FIG. 9 is a flowchart showing a thermal cycle process according to an example 1.

In this example, a shuttle PCR in which fluorescence detection is utilized using the thermal cycler 2 of the modified example 1 will be described below with reference to FIG. 9. The embodiment described above and each of the modified examples may also be applicable to this example. FIG. 9 is a flowchart showing a thermal cycle process according to the present example. Compared with the flowchart in FIG. 5, some differences may be noticeable including S201 and S202. A fluorescence detector 40 used in this example is FLE1000 (produced by Nippon Sheet Glass Co., Ltd.).

A biotip 100 of the example is cylinder-shaped and includes a channel 110 of a tubular form having an internal diameter of 2 mm and a length of 25 mm. The biotip 100 is made of polypropylene resin having heat resistance property of 100 degrees and above. The channel 110 has approximately 130 microliters of dimethyl silicone oil (KF-96L-2cs, produced by Shin-Etsu Chemical Co., Ltd.) filled inside. The reaction mixture 140*a* in this example is a mixture of 1 microliters of human beta-actin DNA (with DNA amount of 10^3 (ten to the third power) copies/microliters), 10 microliters of PCR Master Mix (GeneAmp (registered trademark) Fast PCR Master Mix (2×), produced by Applied Biosystems Inc.), 1 microliters of primer and probe (Pre-Developed TaqMan (registered trademark) Assay Reagents Human ACTB, produced by Applied Biosystems Inc.), and 8 microliters of PCR Water (Water, PCR Grade, produced by Roche Diagnostics Corp.). For the DNA, reverse-transcribed cDNA from commercially offered Total RNA (qPCR Human Reference Total RNA, produced by Clontech Laboratories, Inc.) is used.

First, 1 microliters of the reaction mixture 140*a* is introduced to the channel 110 using a micropipette. The reaction mixture 140*a* is an aqueous solution and therefore not immiscible with the above-mentioned dimethyl silicone oil. The reaction mixture 140*a* is held inside the liquid 130 in a spherical droplet with an approximate diameter of 1.5 mm. The above-mentioned dimethyl silicone oil has a specific gravity of approximately 0.873 at 25 degrees Celsius, and hence the reaction mixture 140*a* (having a specific gravity of 1.0) is in the lowest part of the channel 110 with respect to the gravitational force direction. Then one end of the channel 110 is sealed with a seal (seal 120), and the thermal cycle process is started.

First, the biotip 100 in the present example is placed in the holder 11 of the thermal cycler 2 (S101). In this example, 14 biotips 100 are used. The current disposition of the holder 11 and the first heating unit 12 is the second disposition. The reaction mixture 140*a* is in the second portion 112, or in the closer side to the second heating unit 13. The lid 50 is used to cover the holder 11. When the thermal cycler 2 is operated, S201 is performed.

In S201, the fluorescence detector 40 performs fluorescence measurement. In this example, measurement window 18 faces the fluorescence detector 40 in the second disposition. Thus, when the fluorescence detector 40 is turned on while the holder 11, the first heating unit 12, and the second heating unit 13 are in the second disposition, the fluorescence measurement is performed via the measurement window 18. In this example, the fluorescence detector 40 slides along the slide 22 to perform the measurement for every biotip 100 in an orderly manner. In S201, when measurements have been taken for every biotip 100, S207 is performed. In this example, when the measurements have been taken via all the measurement windows 18, the process proceeds to the S207.

In S207, the disposition is switched from the second disposition to the first disposition. That is to say that S207 is substantially the same with S107 in the embodiment. Switching the disposition holds the holder 11, the first heating unit 12, and the second heating unit 13 in the first disposition, and hence the reaction mixture 140*a* moves to the first portion 111.

Then S102 and S202 are performed. In S102, the first heating unit 12 and the second heating unit 13 heat the biotip 100. In this example, the first temperature is set at 95 degrees Celsius, and the second temperature is set at 66 degrees Celsius. Thus, the temperature of the biotip 100 gradually lowers from the first portion 111, which is heated to 95 degrees Celsius, towards the second portion 112, which is heated to 66 degrees Celsius, forming a temperature gradient. In S102, the reaction mixture 140*a* is in the first portion 111 and hence is heated to 95 degrees Celsius.

In S202, a determination is made whether a third period of time has passed in the first disposition. Given the size of the biotip 100 in this example, the time it takes from starting to heat up to forming a temperature gradient is short enough to ignore, and thus clocking of the third period of time may be started when the biotip 100 is starting to get heated. The third period of time in this example is 10 seconds, at which a hot start in PCR is performed in S202. A hot start is a process that enables DNA amplification by activating DNA polymerase included in the reaction mixture 140*a* by heat. If it is determined that 10 seconds has not yet passed (no), then S202 is repeated. If it is determined that 10 seconds has passed (yes), then the process proceeds to S103.

In S103, a determination is made whether the first period of time has passed in the first disposition. In this example, the first period of time is 1 second. In other words, a process to denature a double-stranded DNA at 95 degrees Celsius is performed for 1 second. Steps S202 and S103 are both performed under the first temperature, and when S202 is followed by S103, the activation of polymerase and denaturation of DNA are in progress substantially in parallel. In S103, a determination is made whether 1 second has passed in the first disposition. If it is determined that 1 second has not yet passed (no), then S103 is repeated. If it is determined that 1 second has passed (yes), then the driving unit 20 rotates the main unit 10*a* (S104) so as to position the second portion 112 in the lowest part of the biotip 100 with respect to the gravitational force direction. Such rotation makes the reaction mixture 140*a* moved from the portion of 95 degrees Celsius to the portion of 66 degrees Celsius of the channel 110 due to the gravitational force. In this example, it takes 3 seconds for the rotation in S104 to complete. During that time period, the reaction mixture 140*a* moves to the second portion 112. The driving unit 20, controlled by the control unit, stops the operation upon the completion of switching to the second disposition, and then S105 is performed.

In S105, a determination is made whether a second period of time has passed in the second disposition. In this example, the second period of time is for 15 seconds. In other words, annealing and elongation at 66 degrees Celsius take 15 seconds. In S105, a determination is made whether 15 seconds has passed in the second disposition. If it is determined that 15 seconds has not yet passed (no), then S105 is repeated. If it is determined that 15 seconds has passed (yes), then another determination is made whether the number of thermal cycles has reached a predetermined number of cycles (S106). In this example, the predetermined number of cycles is 50. In other words, it is determined whether steps S103 to S105 have been completed 50 times. If the number of cycles is smaller than 50, then it is determined that it has not reached the predetermined number of cycles (no), and the process proceeds to S107.

In S107, the driving unit 20 rotates the main unit 10*a* so as to position the first portion 111 in the lowest part of the biotip 100 with respect to the gravitational force direction. Such rotation makes the reaction mixture 140*a* moved from the portion of 66 degrees Celsius to the portion of 95 degrees Celsius of the channel 110 due to the gravitational force. The driving unit 20, controlled by the control unit, stops the operation upon the completion of switching to the first disposition, and then the second thermal cycle starts. In other words, the steps S103 to S106 are repeated again. When it is determined that thermal cycles are applied 50 times (yes) in S106, the fluorescence measurement is performed (S206), and the heating is stopped to end the thermal cycle process.

FIG. 12A is a table of the results from the two fluorescence measurements (S201 and S206). The fluorescent brightness (intensity) before the thermal cycle process is indicated in the column "Before Reaction", and the fluorescent brightness after a predetermined number of the thermal cycle process is indicated in the column "After Reaction". Brightness change ratio (%) is obtained by the equation (1).

$$\text{(Brightness Change Ratio)}=100*\{\text{(After Reaction)}-\text{(Before Reaction)}\}/\text{(Before Reaction)} \quad (1)$$

The probe used in this example is TaqMan Probe. This probe has such characteristics that when a nucleic acid sequence is amplified, the fluorescent brightness increases. As shown in FIG. 12A, compared to the measurements before the thermal cycle process, the fluorescent brightness of the reaction mixture 140 shows an increase after the thermal cycle process. The calculated brightness change ratio shows that the nucleic acid sequence has been amplified sufficiently, and therefore it is confirmed that the thermal cycler 2 of this example is able to amplify the nucleic acid sequence.

In this example, the reaction mixture 140*a* is kept at 95 degrees Celsius for 1 second at first, then the driving unit 20 rotates the main unit 10*a* one half turn to keep the reaction mixture 140*a* at 66 degrees Celsius for 15 seconds. The driving unit 20 rotates the main unit 10*a* another half turn to keep the reaction mixture 140*a* at 95 degrees Celsius. In other words, the driving unit 20 switches the disposition of the holder 11, the first heating unit 12, and the second heating unit 13, thereby keeping the reaction mixture 140*a* in the first disposition or in the second disposition for a desired period of time. Thus, even when the first period of time and the second period of time differ in the thermal cycle process, the heating time periods are readily controllable, thereby enabling to apply desired thermal cycles to the reaction mixture 140*a*.

In this example, the reaction mixture 140*a* is heated for 1 second at the first temperature, for 15 seconds at the second temperature, and takes 3 seconds to move between the first portion 111 and the second portion 112 (a total of 6 seconds for a round trip), indicating that it requires 22 seconds to complete one cycle. Thus, if 50 times of cycles are to be applied, it will take approximately 19 minutes to complete the thermal cycle process including the hot start activation time.

Example 2

One-Step RT PCR

Figures 10, 11:
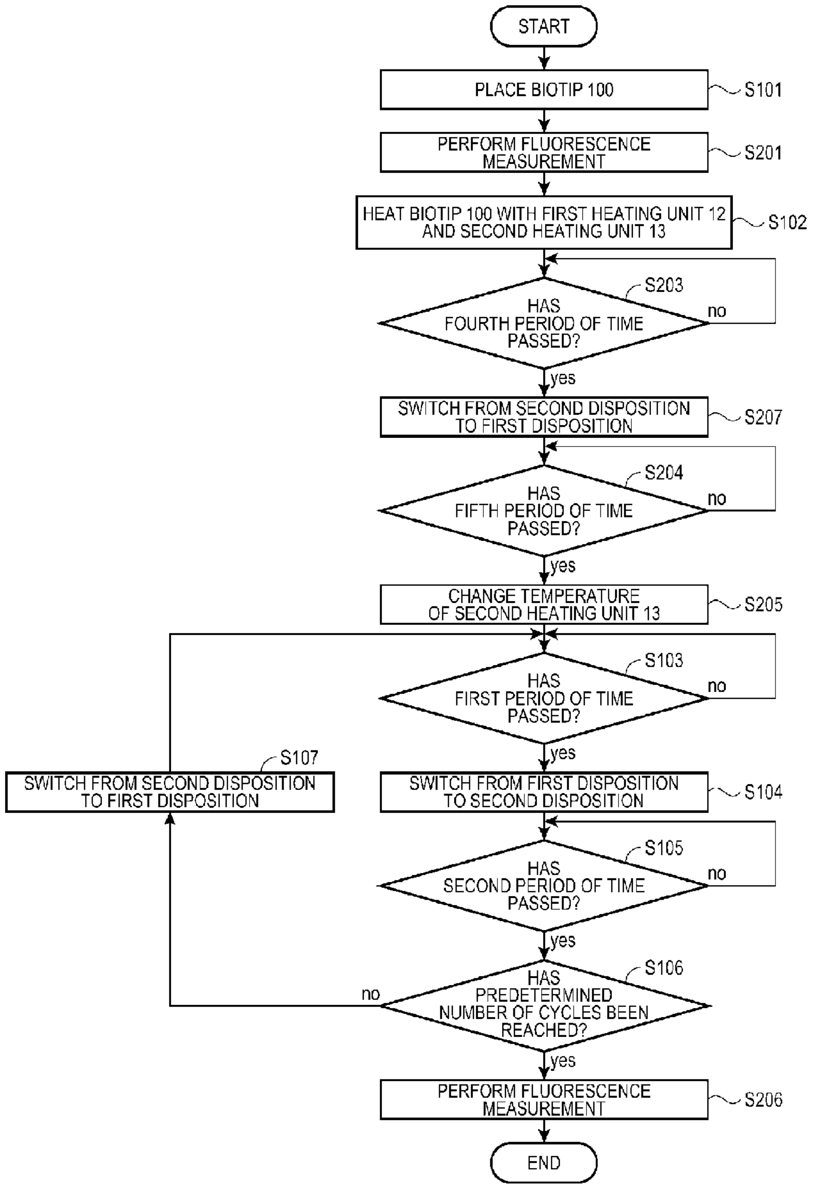
FIG. 10 is a flowchart showing a thermal cycle process according to an example 2.
FIG. 11 is a table showing compositions of the reaction mixture according to the example 2.

In this example, a one-step RT-PCR using the thermal cycler according to the modified examples 1 and 2 will be described with reference to FIG. 10. FIG. 10 is a flowchart showing a thermal cycle process according to the present example. The thermal cycler used in this example functions substantially the same way as the thermal cycler 2 in Example 1 except that the thermal cycler of this example changes the temperature of the second heating unit 13 in middle of the process. The other configurations of each of the modified examples described above are also applicable to this example. A fluorescence detector 40 used in this example is 2104 EnVision Multilabel Counter (produced by Perkin Elmer Inc.).

An RT-PCR (reverse transcription-polymerase chain reaction) is a method to detect RNA or determine quantity of RNA. Reverse transcriptase is used at 45 degrees Celsius to make DNA from an RNA template, and the reverse-transcribed cDNA that has been made will be amplified in PCR. In an RT-PCR in general, a process of reverse transcription and a process of PCR are separate independent processes, and in between these processes, replacing containers and adding reagent are often performed. As opposed to that, in a one-step RT-PCR, reagent exclusive for this purpose is used to conduct reactions of reverse transcription and PCR in a continuous manner. This example uses a one-step RT-PCR as an example, and hence differences between the process in this example and the shuttle PCR process in the example 1 are seen in the reverse transcription steps (S203 to S204) and the transferring step to the shuttle PCR (S205).

The biotip 100 of the present example is substantially the same as that of the example 1, except the constituents of the reaction mixture 140*b*. For the reaction mixture 140*b*, a commercially offered kit for One-Step RT-PCR (One Step SYBR (registered trademark) PrimeScript (registered trademark) PLUS RT-PCR Kit, produced by TAKARA BIO INC.) is used, with its composition adjusted in accordance with FIG. 11.

Similarly to the example 1, three biotips 100 with the reaction mixture 140*b* introduced therein are used to conduct the reaction. In S101, the biotip 100 is placed in the holder 11. Starting the thermal cycler initiates S201, and the measurements of the fluorescent brightness of the reaction mixture 140*b* before the thermal cycle process are taken.

Following that, S102 and S203 are started. In S102 of this example, the first heating unit 12 heats the first portion 111 of the biotip 100 to 95 degrees Celsius, and the second heating unit 13 heats the second portion 112 to 42 degrees Celsius. In this example, the disposition of the holder 11, the first heating unit 12, and the second heating unit 13 in S101 is the second disposition. Thus the reaction mixture 140*b* is in the second portion 112 and heated to 42 degrees Celsius, and the reverse transcription from RNA to DNA occurs.

In S203, a determination is made whether a fourth period of time has passed in the second disposition. This step is substantially the same as S105, except the time period subjected to the determination. In this example, the fourth period of time is for 300 seconds. In S203, when it is determined that 300 seconds has not yet passed (no), S203 is repeated. When it is determined that 300 seconds has passed (yes), then the process proceeds to S207.

In S207, switching the disposition of the holder 11, the first heating unit 12, and the second heating unit 13 from the second disposition to the first disposition initiates S204.

In S204, a determination is made whether a fifth period of time has passed in the first disposition. S204 is substantially the same with S103, except the time period it takes for the determination. In this example, the fifth period of time is for 10 seconds. The first portion 111 is heated to 95 degrees Celsius, and hence the reaction mixture 140*b* moved to the first portion 111 in S207 is heated to 95 degrees Celsius. Heating at 95 degrees Celsius for 10 seconds deactivates the reverse transcriptase. In S204, when it is determined that 10 seconds has not yet passed (no), then S204 is repeated. When it is determined that 10 seconds has passed (yes), then the process proceeds to S205.

S205 is a step in which the temperature, to which the second heating unit 13 heats the biotip 100, is changed. In this example, the second heating unit 13 heats the biotip 100 so as to make the second portion 112 at the temperature of 60 degrees Celsius. Thus the first portion 111 is at 95 degrees Celsius and the second portion 112 is at 60 degrees Celsius, and hence a temperature gradient appropriate for a shuttle PCR is formed in the channel 110 of the biotip 100. After the temperature of the second heating unit 13 is changed in S205, the process proceeds to S103.

In a case where S205 is followed by S103, a determination is made whether the first period of time has passed since S205 was completed. S103 may be initiated if the temperature measured by the temperature sensor shows the desired temperature. In this example, the time it takes to change the temperature is short enough to ignore, so S205 and S103 are initiated at the same time. When S107 is followed by S103, then S103 is substantially the same with the embodiment and the example 1.

The rest of the process after S103 is substantially the same with the example 1, except the specific reaction conditions for the thermal cycle process. Repeating S103 through S107 performs the shuttle PCR. Specifically, a thermal cycle having property of 95 degrees Celsius for 5 seconds and 60 degrees Celsius for 30 seconds is repeated 40 times in the process substantially the same with the example 1 to amplify the DNA.

FIG. 12B is a table of the results from the two fluorescence measurements (S201 and S206). Similarly to the example 1, brightness change ratio is calculated. The probe used in this example is SYBR Green I. This probe also has such characteristics that when a nucleic acid sequence is amplified, the fluorescent brightness increases. As shown in FIG. 12B, compared to the measurements before the thermal cycle process, the fluorescent brightness of the reaction mixture 140 shows an increase after the thermal cycle process. The calculated brightness change ratio shows that the nucleic acid sequence has been amplified sufficiently, and therefore it is confirmed that the thermal cycler 2 of this example is able to amplify the nucleic acid sequence.

In this example, changing the heating temperature in middle of the process enables to heat the reaction mixture 140*b* at the changed temperature. Thus, in addition to the advantages provided by the example 1 (shuttle PCR), this example presents advantages in that a single cycler is able to handle the treatments involving differing heating temperatures without having to increase the number of heating units or complicating the structure of the cycler. Furthermore, changing a time period for which the biotip 100 is held in the first disposition or in the second disposition enables to conduct the reaction that requires a change in the heating period of time in middle of the process, without complicating the structure of the cycler or biotip.

The invention is not limited to the embodiment described above, and still various variations are available. For example, the scope of the invention includes a structure that is substantially the same (for example, its function, method, and result are substantially the same, or its objective and its effect are substantially the same as the invention). The scope of the invention also includes a replaceable structure that is immaterial to the structure described in the embodiment. The scope of the invention further includes a structure that brings about the same functionality and effect, and/or that achieves the same objective. The scope of the invention also includes the structure described in the embodiment with any known structure added thereto.

The invention claimed is:

1. A thermal cycler comprising:

a holder that holds a biotip filled with a reaction mixture and liquid having a smaller specific gravity than the reaction mixture and being immiscible with the reaction mixture, the biotip including a channel in which the reaction mixture moves in proximity to internal facing wall sections;

a heating unit that heats a first portion of the channel when the biotip is in the holder; and a driving unit that disposes the holder and the heating unit by making a switch between a first disposition and a second disposition, the first disposition being such that the first portion is in a lowest part of the channel with respect to a gravitational force direction when the biotip is in the holder, the second disposition being such that a second portion of the channel that is a different portion from the first portion relative to a moving direction of the reaction mixture is in the lowest part of the channel with respect to the gravitational force direction when the biotip is in the holder.

2. The thermal cycler according to claim 1, wherein the driving unit rotates the holder and the heating unit in one direction when switching from the first disposition to the second disposition and in the opposite direction when switching from the second disposition to the first disposition.

3. The thermal cycler according to claim 1, wherein the driving unit makes a switch from the first disposition to the second disposition when a first period of time has passed while keeping the first disposition, and makes a switch from the second disposition to the first disposition when a second period of time has passed while keeping the second disposition.

4. The thermal cycler according to claim 1, wherein the holder holds the biotip in which the reaction mixture moves in a longitudinal direction of the channel, the first portion is a portion that includes one end of the channel in the longitudinal direction, and the second portion is a portion that includes the other end of the channel in the longitudinal direction.

5. The thermal cycler according to claim 1, further comprising a second heating unit that heats the second portion when the biotip is in the holder, wherein the heating unit heats the first portion to a first temperature, and the second heating unit heats the second portion to a second temperature that is different from the first temperature.

6. The thermal cycler according to claim 5, wherein the first temperature is higher than the second temperature.

7. The thermal cycler according to claim 6, wherein the first period of time is shorter than the second period of time.

8. A thermal cycle method comprising:

placing in a holder a biotip filled with a reaction mixture and liquid having a smaller specific gravity than the reaction mixture and being immiscible with the reaction mixture, the biotip including a channel in which the reaction mixture moves in proximity to internal facing wall sections;

disposing the biotip in a first disposition in which a first portion of the channel is in a lowest part of the channel with respect to a gravitational force direction;

heating the first portion of the channel; and disposing the biotip in a second disposition in which a second portion that is a different portion from the first portion relative to a moving direction of the reaction mixture is in the lowest part of the channel with respect to the gravitational force direction.

9. The thermal cycler according to claim 2, wherein the driving unit makes a switch from the first disposition to the second disposition when a first period of time has passed while keeping the first disposition, and makes a switch from the second disposition to the first disposition when a second period of time has passed while keeping the second disposition.

10. The thermal cycler according to claim 2, wherein the holder holds the biotip in which the reaction mixture moves in a longitudinal direction of the channel, the first portion is a portion that includes one end of the channel in the longitudinal direction, and the second portion is a portion that includes the other end of the channel in the longitudinal direction.

11. The thermal cycler according to claim 3, wherein the holder holds the biotip in which the reaction mixture moves in a longitudinal direction of the channel, the first portion is a portion that includes one end of the channel in the longitudinal direction, and the second portion is a portion that includes the other end of the channel in the longitudinal direction.

12. The thermal cycler according to claim 2, further comprising a second heating unit that heats the second portion when the biotip is in the holder, wherein the heating unit heats the first portion to a first temperature, and the second heating unit heats the second portion to a second temperature that is different from the first temperature.

13. The thermal cycler according to claim 3, further comprising a second heating unit that heats the second portion when the biotip is in the holder, wherein the heating unit heats the first portion to a first temperature, and the second heating unit heats the second portion to a second temperature that is different from the first temperature.

14. The thermal cycler according to claim 4, further comprising a second heating unit that heats the second portion when the biotip is in the holder, wherein the heating unit heats the first portion to a first temperature, and the second heating unit heats the second portion to a second temperature that is different from the first temperature.

15. The thermal cycler according to claim 12, wherein the first temperature is higher than the second temperature.

16. The thermal cycler according to claim 13, wherein the first temperature is higher than the second temperature.

17. The thermal cycler according to claim 14, wherein the first temperature is higher than the second temperature.

18. The thermal cycler according to claim 15, wherein the first period of time is shorter than the second period of time.

19. The thermal cycler according to claim 16, wherein the first period of time is shorter than the second period of time.

20. The thermal cycler according to claim 17, wherein the first period of time is shorter than the second period of time.

* * * * *